(12) United States Patent
Drapeau et al.

(10) Patent No.: US 9,744,124 B2
(45) Date of Patent: *Aug. 29, 2017

(54) FLOWABLE COMPOSITION THAT HARDENS ON DELIVERY TO A TARGET TISSUE SITE BENEATH THE SKIN

(71) Applicant: Warsaw Orthopedic, Inc., Warsaw, IN (US)

(72) Inventors: Susan J. Drapeau, Cordova, TN (US); William F. McKay, Memphis, TN (US); Nelson Scarborough, Andover, MA (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/886,760

(22) Filed: Oct. 19, 2015

(65) Prior Publication Data

US 2016/0038407 A1 Feb. 11, 2016

Related U.S. Application Data

(62) Division of application No. 12/262,705, filed on Oct. 31, 2008, now Pat. No. 9,161,903.

(51) Int. Cl.
| | | |
|---|---|---|
| A61K 9/00 | (2006.01) |
| A61K 31/573 | (2006.01) |
| A61K 47/10 | (2017.01) |
| A61K 47/34 | (2017.01) |
| A61K 51/12 | (2006.01) |
| A61K 9/16 | (2006.01) |

(52) U.S. Cl.
CPC .......... *A61K 9/0024* (2013.01); *A61K 9/0085* (2013.01); *A61K 9/16* (2013.01); *A61K 31/573* (2013.01); *A61K 47/10* (2013.01); *A61K 47/34* (2013.01); *A61K 51/1213* (2013.01)

(58) Field of Classification Search
None
See application file for complete search history.

(56) References Cited

U.S. PATENT DOCUMENTS

| | | | | |
|---|---|---|---|---|
| 5,212,162 A * | 5/1993 | Missel | ................. | A61K 9/0048 424/427 |
| 5,324,519 A * | 6/1994 | Dunn | ................. | A61K 9/0024 424/422 |
| 5,744,153 A * | 4/1998 | Yewey | ................. | A61K 9/0024 424/422 |
| 6,004,573 A * | 12/1999 | Rathi | ................. | A61K 9/0024 424/426 |
| 6,069,129 A | 5/2000 | Sandberg et al. | | |
| 6,179,862 B1 | 1/2001 | Sawhney | | |
| 6,287,588 B1 * | 9/2001 | Shih | ................. | A61K 47/34 424/426 |
| 6,331,311 B1 | 12/2001 | Brodbeck et al. | | |
| 6,416,776 B1 * | 7/2002 | Shamie | ................. | A61F 2/441 424/422 |
| 6,428,804 B1 | 8/2002 | Suzuki et al. | | |
| 6,461,631 B1 | 10/2002 | Dunn et al. | | |
| 6,589,549 B2 | 7/2003 | Shih et al. | | |
| 6,630,155 B1 | 10/2003 | Chandrashekar et al. | | |
| 6,632,457 B1 | 10/2003 | Sawhney | | |
| 6,773,714 B2 | 8/2004 | Dunn et al. | | |
| 2002/0009454 A1 | 1/2002 | Boone et al. | | |
| 2002/0090398 A1 | 7/2002 | Dunn et al. | | |
| 2004/0072799 A1 | 4/2004 | Li et al. | | |
| 2004/0082540 A1 | 4/2004 | Hermida Ochoa | | |
| 2004/0214793 A1 | 10/2004 | Hermida Ochoa | | |
| 2004/0228794 A1 * | 11/2004 | Weller | ................. | A61K 9/0019 424/1.11 |
| 2005/0142163 A1 | 6/2005 | Hunter et al. | | |
| 2005/0186261 A1 | 8/2005 | Avelar et al. | | |
| 2005/0197293 A1 | 9/2005 | Mellis et al. | | |
| 2006/0148903 A1 | 7/2006 | Burch et al. | | |
| 2006/0189944 A1 | 8/2006 | Campbell et al. | | |
| 2007/0156180 A1 | 7/2007 | Jaax et al. | | |
| 2007/0202074 A1 | 8/2007 | Shalaby | | |
| 2007/0243225 A1 | 10/2007 | McKay | | |
| 2007/0243228 A1 | 10/2007 | McKay | | |
| 2008/0091207 A1 | 4/2008 | Truckai et al. | | |

FOREIGN PATENT DOCUMENTS

WO 03005961 1/2003

OTHER PUBLICATIONS

Atrigel Development Sheet.
U.S. Appl. No. 12/056,511, filed Mar. 27, 2008.

* cited by examiner

*Primary Examiner* — Susan Tran
*Assistant Examiner* — William Craigo

(57) ABSTRACT

Flowable compositions and methods are provided for delivering a therapeutic agent at or near a target tissue site beneath the skin of a patient, the flowable composition comprising (i) a solvent and (ii) an effective amount of the therapeutic agent, the flowable composition being capable of hardening to form a drug depot at a physiological temperature or as solvent contacts bodily fluid at or near the target tissue site, wherein the drug depot is capable of releasing the therapeutic agent over a period of at least one day and the target tissue site comprises at least one muscle, ligament, tendon, cartilage, spinal disc, spinal foraminal space near the spinal nerve root, facet or synovial joint, or spinal canal. In some embodiments, an implantable drug depot for delivering a therapeutic agent is provided, the implantable drug depot comprising (i) a chamber; and (ii) a flowable composition comprising an effective amount of a therapeutic agent disposed within the chamber of the drug depot, the flowable composition capable of hardening when the drug depot is delivered at or near the target tissue site.

13 Claims, 6 Drawing Sheets

FLOWABLE COMPOSITION THAT HARDENS ON DELIVERY TO A TARGET TISSUE SITE BENEATH THE SKIN

This application is a divisional application of U.S. patent application Ser. No. 12/262,705 filed Oct. 31, 2008, entitled "FLOWABLE COMPOSITION THAT HARDENS ON DELIVERY TO A TARGET TISSUE SITE BENEATH THE SKIN," the contents of which are incorporated in its entirety by reference herein.

BACKGROUND

Localized delivery of therapeutic agents (e.g., intrathecally, intraspinally, intraarticularly, etc.) has become increasingly more popular over the years because it has several advantages over more conventional routes of drug delivery such as oral delivery. Localized delivery has the advantage of allowing the therapeutic agent to be implanted directly at the site where drug action is needed. This becomes especially important for drugs that have unwanted systemic side effects.

Localized delivery of therapeutic agents protects the therapeutic agent from breaking down due to harsh physiological environments (e.g., gastric and liver enzymes) and thus improves the drug's stability in vivo. This particular feature makes this technology particularly attractive for the delivery of labile drugs such as proteins and peptides. Localized delivery also improves patient compliance. For example, therapeutic agents can be encapsulated and delivered locally allowing the drug to be released over extended periods (e.g., 6 months or longer) and hence eliminates the need for multiple injections. This feature can improve patient compliance especially for drugs for chronic indications, requiring frequent injections.

In the past, localized repeat delivery of therapeutic agents has been used to treat chronic debilitating diseases such as osteoarthritis. Osteoarthritis is a chronic condition that affects millions of people in the world and is a type of arthritis that is caused by the chronic breakdown and eventual loss of cartilage in one or more joints. Osteoarthritis often affects synovial joints, such as the knees, hips, fingers, thumbs, neck, and spine. Severe forms of the disease are extremely disabling and restrict a patient's lifestyle. Localized delivery via intraarticular injection of corticosteroids, hyaluronan or hylan provide some short term relief in controlling the pain symptoms of osteoarthritis.

Sciatica, another chronic debilitating disease, can be a painful condition associated with the sciatic nerve which runs from the lower part of the spinal cord (the lumbar region), down the back of the leg and to the foot. Sciatica generally begins with a herniated disc, which later leads to local immune system activation. The herniated disc also may damage the nerve root by pinching or compressing it, leading to additional immune system activation in the area. In the past, localized delivery of corticosteroids (e.g., epidural) has been used to provide short term relief of the inflammation and pain associated with sciatica.

Newer methods are currently being investigated for treatment of chronic debilitating diseases utilizing localized delivery of drug depots. In these treatments typically the drug depot is delivered locally to the treatment site and the drug is released from the depot in a relatively uniform dose over weeks, months or even years. Localized delivery of drug depots is becoming especially important and popular in modulating the immune, inflammation and/or pain responses in treatment of chronic diseases.

Sometimes after the drug depot is implanted at the treatment site, unfortunately, the drug depot may migrate from the implant site prior to surgical closure (e.g. floats off in blood or shifts as tissues are repositioned during surgical site closure) or as physiological conditions change (e.g., repair and regeneration of cells, tissue in growth, movement at implant site, etc.). At times, this may reduce efficacy of the drug as the drug depot migrates away from the implant site and lodges in a distant site. If this occurs, often the drug depot will have to be removed from the distant site and be reinserted causing additional physical and psychological trauma to a patient. In some cases, if the drug depot migrates into a joint, the drug depot may inhibit movement. In more severe cases, if the drug depot migrates in a blood vessel, it may restrict blood flow causing an ischemic event (e.g., embolism, necrosis, infarction, etc.), which could be detrimental to the patient.

New drug depot compositions and methods are needed, which can easily allow accurate and precise placement of a drug depot with minimal physical and psychological trauma to a patient. When implanting several drug depots at a time, drug depot compositions and methods are needed that accurately and precisely allow placement of the drug depot in a manner that optimizes location, accurate spacing, and drug distribution.

SUMMARY

New drug depot compositions and methods are provided, which can easily allow accurate and precise implantation of a drug depot in situ with minimal physical and psychological trauma to a patient. One advantage of the drug depot compositions and methods is that the drug depot can now be easily delivered to the target tissue site (e.g., synovial joint, at or near the spinal column, etc.) using a flowable composition (e.g., a liquid, gel, suspension, etc.) that hardens upon contact with the target tissue. In this way, accurate and precise implantation of a drug depot in a minimally invasive procedure can be accomplished. Another advantage, in various embodiments, is that by utilizing the flowable composition, implantation of the drug depot can now be accomplished without the need to suture the drug depot to the target site reducing physical and psychological trauma to the patient. In some embodiments, the drug depot is implanted using a confining element (e.g., sheet, strip, ribbon, ring, balloon, chamber, tissue cavity, etc.) that may be deployed at or near the target tissue site. The confining element may be filled with the flowable composition where the therapeutic agent can be confined and released over a period of at least one day.

In some embodiments, a flowable composition is provided for delivering a therapeutic agent at or near a target tissue site beneath the skin of a patient, the flowable composition comprising (i) solvent and (ii) an effective amount of the therapeutic agent, the flowable composition being capable of hardening to form a drug depot at a physiological temperature or as solvent contacts bodily fluid at or near the target tissue site, wherein the drug depot is capable of releasing the therapeutic agent over a period of at least one day and the target tissue site comprises at least one muscle, ligament, tendon, cartilage, spinal disc, spinal foraminal space near the spinal nerve root, facet or synovial joint, or spinal canal.

In some embodiments, an implantable drug depot is provided for delivering a therapeutic agent at or near a target tissue site beneath the skin of a patient, the implantable drug depot comprising (i) a chamber; and (ii) a flowable composition comprising an effective amount of a therapeutic agent disposed within the chamber of the drug depot, the flowable composition capable of hardening when the drug depot is delivered at or near the target tissue site, wherein the drug depot is capable of releasing the therapeutic agent over a period of at least one day.

In some embodiments, a kit is provided for implanting a drug depot at or near a target tissue site beneath the skin of a patient, the kit comprising (i) an implantable drug depot having a chamber disposed within the drug depot; and (ii) a flowable composition comprising an effective amount of a therapeutic agent, the flowable composition capable of hardening inside the chamber of the drug depot when the drug depot is implanted at or near the target tissue site; wherein the drug depot is capable of releasing the therapeutic agent over a period of at least one day.

In some embodiments, a method is provided for delivering a therapeutic agent into a target tissue site beneath the skin, the method comprising inserting a cannula at or near a target tissue site and injecting a flowable composition comprising (i) a solvent and (ii) an effective amount of the therapeutic agent, the flowable composition being capable of hardening to form a drug depot at a physiological temperature or as solvent contacts bodily fluid at or near the target tissue site, wherein the drug depot is capable of releasing the therapeutic agent over a period of at least one day and the target tissue site comprises at least one muscle, ligament, tendon, cartilage, spinal disc, spinal foraminal space near the spinal nerve root, facet or synovial joint, or spinal canal.

In some embodiments, a method is provided for delivering a therapeutic agent at or near a target tissue site beneath the skin, the method comprising inserting a cannula at or near a target tissue site and administering a drug depot comprising a chamber; and filling the chamber with a flowable composition comprising an effective amount of a therapeutic agent, the flowable composition capable of hardening at or near the target tissue site, wherein the drug depot is capable of releasing the therapeutic agent over a period of at least one day.

In some embodiments, a low profile drug depot is utilized that does not substantially interfere with movement of the joint.

Additional features and advantages of various embodiments will be set forth in part in the description that follows, and in part will be apparent from the description, or may be learned by practice of various embodiments. The objectives and other advantages of various embodiments will be realized and attained by means of the elements and combinations particularly pointed out in the description and appended claims.

BRIEF DESCRIPTION OF THE DRAWINGS

In part, other aspects, features, benefits and advantages of the embodiments will be apparent with regard to the following description, appended claims and accompanying drawings where:

Figure 1:
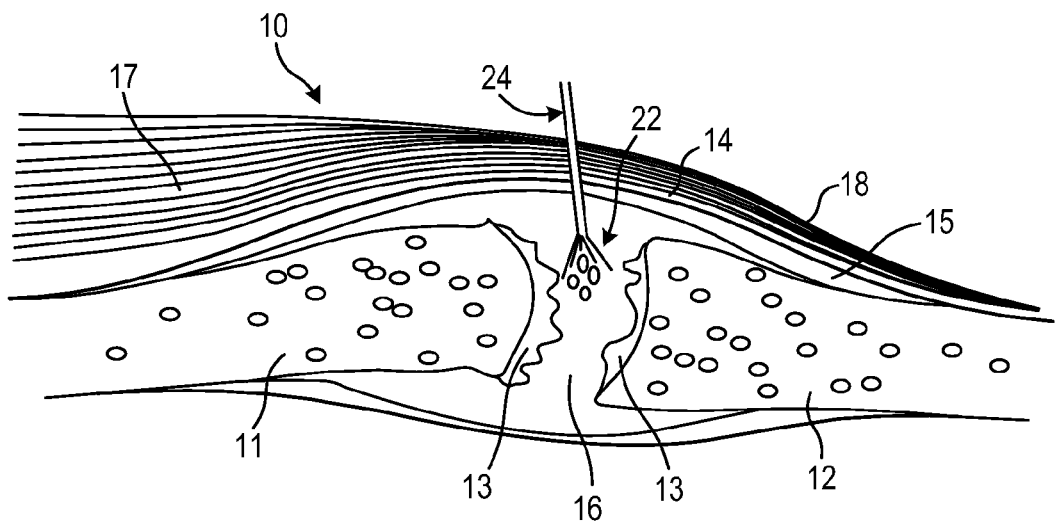
FIG. 1 illustrates a side sectional view of a joint affected by osteoarthritis and delivery of an embodiment of a flowable composition containing a therapeutic agent dispersed therein that can be administered into the synovial joint via a cannula or needle.

It is to be understood that the figures are not drawn to scale. Further, the relation between objects in a figure may not be to scale, and may in fact have a reverse relationship as to size. The figures are intended to bring understanding and clarity to the structure of each object shown, and thus, some features may be exaggerated in order to illustrate a specific feature of a structure.

DETAILED DESCRIPTION

For the purposes of this specification and appended claims, unless otherwise indicated, all numbers expressing quantities of ingredients, percentages or proportions of materials, reaction conditions, and other numerical values used in the specification and claims, are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth, the broad scope of the invention are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all subranges subsumed therein. For example, a range of "1 to 10" includes any and all subranges between (and including) the minimum value of 1 and the maximum value of 10, that is, any and all subranges having a minimum value of equal to or greater than 1 and a maximum value of equal to or less than 10, e.g., 5.5 to 10.

It is noted that, as used in this specification and the appended claims, the singular forms "a," "an," and "the," include plural referents unless expressly and unequivocally limited to one referent. Thus, for example, reference to "a drug depot" includes one, two, three or more drug depots.

Reference will now be made in detail to certain embodiments of the invention, examples of which are illustrated in the accompanying drawings. While the invention will be described in conjunction with the illustrated embodiments, it will be understood that they are not intended to limit the invention to those embodiments. On the contrary, the invention is intended to cover all alternatives, modifications, and equivalents, which may be included within the invention as defined by the appended claims.

The headings below are not meant to limit the disclosure in any way; embodiments under any one heading may be used in conjunction with embodiments under any other heading.

New drug depot compositions and methods are provided, which can easily allow accurate and precise implantation of a drug depot with minimal physical and psychological trauma to the patient. The drug depot compositions and methods provided utilize a flowable composition (e.g., gel, suspension, solution) that hardens on contact with the target tissue site. In this way, accurate and precise implantation of a drug depot in a minimally invasive procedure can be accomplished. In various embodiments, the flowable composition avoids the need to suture the drug depot to the target site reducing physical and psychological trauma to the patient. In various embodiments, when several drug depots are to be implanted, the flowable composition allows accurate placement of the drug depot in a manner to optimize location, accurate spacing, and drug distribution.

In some embodiments, a confining element (e.g., sheet, strip, ribbon, ring, balloon, chamber, tissue cavity, etc.) that may be deployed at or near the target tissue site and the flowable composition filled in the confining element.

In some embodiments, a flowable composition is provided for delivering a therapeutic agent at or near a target tissue site beneath the skin of a patient, the flowable composition comprising (i) a solvent and (ii) an effective amount of the therapeutic agent, the flowable composition being capable of hardening to form a drug depot at a physiological temperature or as solvent contacts bodily fluid at or near the target tissue site, wherein the drug depot is capable of releasing the therapeutic agent over a period of at least one day and the target tissue site comprises at least one muscle, ligament, tendon, cartilage, spinal disc, spinal foraminal space near the spinal nerve root, facet or synovial joint, or spinal canal.

Flowable compositions include liquid (e.g., solution, suspension, or the like) or semi-solid compositions (e.g., gels) that are easy to manipulate and may be brushed, sprayed, dripped, injected, shaped and/or molded at or near the target tissue site as it coagulates. "Flowable" includes formulations with a low viscosity or water-like consistency to those with a high viscosity, such as a paste-like material. In various embodiments, the flowability of the formulation allows it to conform to irregularities, crevices, cracks, and/or voids in the tissue site. For example, in various embodiments, the formulation may be used to fill one or more voids in an osteolytic lesion. Upon contact with an aqueous medium (e.g., body fluid, water, etc.), the flowable composition hardens to form a drug depot that controls drug release.

In these applications, a therapeutic agent is added to the flowable composition so that when the flowable composition hardens to form the drug depot inside the body, the therapeutic agent is released in a sustained manner through the polymer matrix of the drug depot, by direct dissolution, degradation and/or erosion of the drug depot.

Drug Depot

A drug depot comprises a physical structure to facilitate sustained release of the drug in a desired site (e.g., a synovial joint, a disc space, a spinal canal, a tissue of the patient, etc.). The drug depot also comprises the drug. The term "drug" as used herein is generally meant to refer to any substance that alters the physiology of a the patient. The term "drug" may be used interchangeably herein with the terms "therapeutic agent", "therapeutically effective amount", and "active pharmaceutical ingredient" or "API". It will be understood that a "drug" formulation may include more than one therapeutic agent, wherein exemplary combinations of therapeutic agents include a combination of two or more drugs. The drug depot can provide a concentration gradient of the therapeutic agent around the depot for delivery to the site. In various embodiments, the drug depot provides an optimal drug concentration gradient of the therapeutic agent at a distance of up to about 1 mm to about 5 cm from the implant site.

A "therapeutically effective amount" or "effective amount" is such that when administered, the drug results in alteration of the biological activity, such as, for example, inhibition of inflammation, reduction or alleviation of pain, improvement in the condition, etc. The dosage administered to a patient can be as single or multiple doses depending upon a variety of factors, including the drug's administered pharmacokinetic properties, the route of administration, patient conditions and characteristics (sex, age, body weight, health, size, etc.), extent of symptoms, concurrent treatments, frequency of treatment and the effect desired.

Examples of therapeutic agents include, those that are direct- and local-acting modulators of pro-inflammatory cytokines such as TNF-$\alpha$ and IL-1 including, but not limited to, soluble tumor necrosis factor $\alpha$ receptors, any pegylated soluble tumor necrosis factor $\alpha$ receptor, monoclonal or polyclonal antibodies or antibody fragments or combinations thereof. Examples of suitable therapeutic agents include receptor antagonists, molecules that compete with the receptor for binding to the target molecule, antisense polynucleotides, and inhibitors of transcription of the DNA encoding the target protein. Suitable examples include but are not limited to Adalimumab, Infliximab, Etanercept, Pegsunercept (PEG sTNF-R1), sTNF-R1, CDP-870, CDP-571, CNI-1493, RDP58, ISIS 104838, 1→3-$\beta$-D-glucans, Lenercept, PEG-sTNFRII Fc Mutein, D2E7, Afelimomab, and combinations thereof. In other embodiments, a therapeutic agent includes metalloprotease inhibitors, glutamate antagonists, glial cell-derived neurotropic factors (GDNF), B2 receptor antagonists, Substance P receptor (NK1) antagonists such as capsaicin and civamide, downstream regulatory element antagonistic modulator (DREAM), iNOS, inhibitors of tetrodotoxin (TTX)-resistant Na+-channel receptor subtypes PN3 and SNS2, inhibitors of interleukins such as IL-1, IL-6 and IL-8, and anti-inflammatory cytokines, TNF binding protein, onercept (r-hTBP-1), recombinant adeno-associated viral (rAAV) vectors encoding inhibitors, enhancers, potentiators, or neutralizers, antibodies, including but not limited to naturally occurring or synthetic, double-chain, single-chain, or fragments thereof. For example, suitable therapeutic agents include molecules that are based on single chain antibodies called Nanobodies™ (Ablynx, Ghent Belgium), which are defined as the smallest functional fragment of a naturally occurring, single-domain antibody. Alternatively, therapeutic agents include, agents that effect kinases and/or inhibit cell signaling mitogen-activated protein kinases (MAPK), p38 MAPK, Src or protein tyrosine kinase (PTK). Therapeutic agents include, kinase inhibitors such as, for example, Gleevec, Herceptin, Iressa, imatinib (STI571), herbimycin A, tyrphostin 47, erbstatin, genistein, staurosporine, PD98059, SB203580, CNI-1493, VX-50/702 (Vertex/Kissei), SB203580, BIRB 796 (Boehringer Ingelheim), Glaxo P38 MAP Kinase inhibitor, RWJ67657 (J&J), UO126, Gd, SCIO-469 (Scios), RO3201195 (Roche), Semipimod (Cytokine PharmaSciences), or derivatives thereof.

Therapeutic agents, in various embodiments, block the transcription or translation of TNF-α or other proteins in the inflammation cascade. Suitable therapeutic agents include, but are not limited to, integrin antagonists, alpha-4 beta-7 integrin antagonists, cell adhesion inhibitors, interferon gamma antagonists, CTLA4-Ig agonists/antagonists (BMS-188667), CD40 ligand antagonists, Humanized anti-IL-6 mAb (MRA, Tocilizumab, Chugai), HMGB-1 mAb (Critical Therapeutics Inc.), anti-IL2R antibodies (daclizumab, basilicimab), ABX (anti IL-8 antibodies), recombinant human IL-10, or HuMax IL-15 (anti-IL 15 antibodies).

Other suitable therapeutic agents include IL-1 inhibitors, such Kineret® (anakinra) which is a recombinant, non-glycosylated form of the human inerleukin-1 receptor antagonist (IL-1Ra), or AMG 108, which is a monoclonal antibody that blocks the action of IL-1. Therapeutic agents also include excitatory amino acids such as glutamate and aspartate, antagonists or inhibitors of glutamate binding to NMDA receptors, AMPA receptors, and/or kainate receptors. Interleukin-1 receptor antagonists, thalidomide (a TNF-α release inhibitor), thalidomide analogues (which reduce TNF-α production by macrophages), bone morphogenetic protein (BMP) type 2 and BMP-4 (inhibitors of caspase 8, a TNF-α activator), quinapril (an inhibitor of angiotensin II, which upregulates TNF-α), interferons such as IL-11 (which modulate TNF-α receptor expression), and aurin-tricarboxylic acid (which inhibits TNF-α), for example, may also be useful as therapeutic agents for reducing inflammation. It is contemplated that where desirable a pegylated form of the above may be used. Examples of other therapeutic agents include NF kappa B inhibitors such as glucocorticoids, clonidine; antioxidants, such as dilhiocarbamate, and other compounds, such as, for example, sulfasalazine.

Other therapeutic agents can include extracellular matrix proteins that may be critical to the repair of a target tissue. An example would be MIA/CD-RAP (melanoma inhibitory activity/cartilage-derived retinoic-acid-sensitive protein), which is a matrix component for mature and developing cartilage.

Specific examples of therapeutic agents suitable for use include, but are not limited to an anti-inflammatory agent, analgesic agent, or osteoinductive growth factor or a combination thereof. Anti-inflammatory agents include, but are not limited to, salicylates, diflunisal, sulfasalazine, indomethacin, ibuprofen, naproxen, tolmetin, ketorolac, diclofenac, ketoprofen, fenamates (mefenamic acid, meclofenamic acid), enolic acids (piroxicam, meloxicam), nabumetone, celecoxib, etodolac, nimesulide, apazone, gold, sulindac or tepoxalin; antioxidants, such as dithiocarbamate, and other compounds such as sulfasalazine [2-hydroxy-5-[-4-[C2-pyridinylamino)sulfonyl]azo]benzoic acid], steroids, such as fluocinolone, cortisol, cortisone, hydrocortisone, fludrocortisone, prednisone, prednisolone, methylprednisolone, triamcinolone, betamethasone, dexamethasone, beclomethasone, fluticasone or a combination thereof.

Suitable anabolic growth or anti-catabolic growth factors include, but are not limited to, a bone morphogenetic protein, a growth differentiation factor (GDF), a LIM mineralization protein, CDMP or progenitor cells or a combination thereof. Examples include, but are not limited to, BMP-2, rhBMP-2, BMP-3, rhBMP-3, BMP-4 (also referred to as BMP-2B), rhBMP4 (also referred to as rhBMP-2B), BMP-5, rhBMP-5, BMP-6, rhBMP-6, BMP-7 (OP-1), rhBMP-7 (rhOP-1), BMP-8, rhBMP-8, BMP-9, rhBMP-9, BMP-12, rhBMP-12, BMP-13, rhBMP-13, BMP-15, rhBMP-15, BMP-16, rhBMP-16, BMP-17, rhBMP-17, BMP-18, rhBMP-18, GDF-1, rhGDF-1, GDF-3, rhGDF-3, GDF-5, rhGDF-5, GDF-6, rhGDF-6, GDF-7, rhGDF-7, GDF-8, rhGDF-8, GDF-9, rhGDF-9, GDF-10, rhGDF-10, GDF-11, rhGDF-11, GDF-12, rhGDF-12, GDF-14, and rhGDF-14.

Suitable analgesic agents include, but are not limited to, acetaminophen, lidocaine, bupivicaine, opioid analgesics such as buprenorphine, butorphanol, dextromoramide, dezocine, dextropropoxyphene, diamorphine, fentanyl, alfentanil, sufentanil, hydrocodone, hydromorphone, ketobemidone, levomethadyl, mepiridine, methadone, morphine, nalbuphine, opium, oxycodone, papaveretum, pentazocine, pethidine, phenoperidine, piritramide, dextropropoxyphene, remifentanil, tilidine, tramadol, codeine, dihydrocodeine, meptazinol, dezocine, eptazocine, flupirtine or a combination thereof.

Analgesics also include agents with analgesic properties, such as for example, amitriptyline, carbamazepine, gabapentin, pregabalin, clonidine, or a combination thereof.

The depot may contain a muscle relaxant. Exemplary muscle relaxants include by way of example and not limitation, alcuronium chloride, atracurium bescylate, baclofen, carbolonium, carisoprodol, chlorphenesin carbamate, chlorzoxazone, cyclobenzaprine, dantrolene, decamethonium bromide, fazadinium, gallamine triethiodide, hexafluorenium, meladrazine, mephensin, metaxalone, methocarbamol, metoc urine iodide, pancuronium, pridinol mesylate, styramate, suxamethonium, suxethonium, thiocolchicoside, tizanidine, tolperisone, tubocuarine, vecuronium, or combinations thereof.

The depot comprises the therapeutic agent or agents and may also contain other non-active ingredients. It has a multi-functional purpose including the carrying, stabilizing and controlling the release of the therapeutic agent(s). The controlled release process, for example, may be by a solution-diffusion mechanism or it may be governed by an erosion-controlled process.

Typically, after the flowable composition hardens into a depot, the depot will be a solid or semi-solid formulation comprising a biocompatible material, which can be biodegradable. "Harden", "cure", "set" are used interchangeably and are defined as the transition from a liquid to solid or from a liquid to a gel.

The term "solid" is intended to mean a rigid material, while, "semi-solid" is intended to mean a material that has some degree of flexibility, thereby allowing the depot to bend and conform to the surrounding tissue requirements. In some embodiments, the liquid composition hardens in situ to form a solid or semi-solid drug depot after implantation. Typically, hardening takes from about 0.25 hours to 12 hours, or from about 0.5 hours to about 8 hours, or from about 1 hour to 4 hours, or from about 1 hour to about 2 hours.

In various embodiments, the depot material will be durable within the tissue site for a period of time equal to (for biodegradable components) or greater than (for non-biodegradable components) the planned period of drug delivery. For example, the depot material may have a melting point or glass transition temperature close to or higher than body temperature, but lower than the decomposition or degradation temperature of the therapeutic agent. However, the pre-determined erosion of the depot material can also be used to provide for sustained release of the loaded therapeutic agent(s).

In various embodiments, the depot may have a high drug loading, such that the therapeutic agent comprises about 5-99 wt % of the depot, or 30-95 wt % of the depot, or 50-95 wt % of the depot. The balance is depot material, including optional inactive materials.

In some instance, it may be desirable to avoid having to remove the drug depot after use. In those instances, the depot may comprise a biodegradable material. There are numerous materials available for this purpose and having the characteristic of being able to breakdown or disintegrate over a prolonged period of time when positioned at or near the target tissue. As function of the chemistry of the biodegradable material the mechanism of the degradation process can be hydrolytical or enzymatical in nature, or both. In various embodiments, the degradation can occur either at the surface (heterogeneous or surface erosion) or uniformly throughout the drug delivery system depot (homogeneous or bulk erosion).

A "depot" includes but is not limited to capsules, sheets, strips, ribbons, microspheres, microparticles, microcapsules, microfibers particles, nanospheres, nanoparticles, coating, matrices, wafers, pills, pellets, emulsions, liposomes, micelles, or other pharmaceutical delivery compositions. Suitable materials for the depot are ideally pharmaceutically acceptable biodegradable and/or any bioabsorbable materials that are preferably FDA approved or GRAS materials. These materials can be polymeric or non-polymeric, as well as synthetic or naturally occurring, or a combination thereof.

The term "biodegradable" includes that all or parts of the flowable composition and/or depot will degrade over time by the action of enzymes, by hydrolytic action and/or by other similar mechanisms in the body. In various embodiments, "biodegradable" includes that the flowable composition and/or depot (e.g., microparticle, microsphere, etc.) can break down or degrade within the body to non-toxic components after or while a therapeutic agent has been or is being released. By "bioerodible" it is meant that the depot and/or flowable composition will erode or degrade over time due, at least in part, to contact with substances found in the surrounding tissue, fluids or by cellular action. By "bioabsorbable" it is meant that the depot and/or flowable composition will be broken down and absorbed within the body, for example, by a cell or tissue. "Biocompatible" means that neither the depot and/or flowable composition will cause substantial tissue irritation or necrosis at the target tissue site.

In various embodiments, the depot may comprise a bioabsorbable, a bioerodible, and/or a biodegradable biopolymer that may provide immediate release, sustained release or controlled release of the drug. Examples of suitable sustained release biopolymers include but are not limited to poly (alpha-hydroxy acids), poly (lactide-co-glycolide) (PLGA), polylactide (PLA), polyglycolide (PG), polyethylene glycol (PEG) conjugates of poly (alpha-hydroxy acids), polyorthoesters, polyaspirins, polyphosphagenes, collagen, starch, pre-gelatinized starch, hyaluronic acid, chitosans, gelatin, alginates, albumin, fibrin, vitamin E analogs, such as alpha tocopheryl acetate, d-alpha tocopheryl succinate, D,L-lactide, or L-lactide, -caprolactone, dextrans, vinylpyrrolidone, polyvinyl alcohol (PVA), PVA-g-PLGA, PEGT-PBT copolymer (polyactive), methacrylates, poly(N-isopropylacrylamide), PEO-PPO-PEO (pluronics), PEO-PPO-PAA copolymers, PLGA-PEO-PLGA, PEG-PLG, PLA-PLGA, poloxamer 407, PEG-PLGA-PEG triblock copolymers, SAIB (sucrose acetate isobutyrate) or combinations thereof.

The depot may optionally contain inactive materials such as buffering agents and pH adjusting agents such as potassium bicarbonate, potassium carbonate, potassium hydroxide, sodium acetate, sodium borate, sodium bicarbonate, sodium carbonate, sodium hydroxide or sodium phosphate; degradation/release modifiers; drug release adjusting agents; emulsifiers; preservatives such as benzalkonium chloride, chlorobutanol, phenylmercuric acetate and phenylmercuric nitrate, sodium bisulfite, sodium bisulfate, sodium thiosulfate, thimerosal, methylparaben, polyvinyl alcohol and phenylethyl alcohol; solubility adjusting agents; stabilizers; and/or cohesion modifiers. Typically, any such inactive materials will be present within the range of 0-75 wt %, and more typically within the range of 0-30 wt %. If the depot is to be placed in the spinal area or joint area, in various embodiments, the depot may comprise sterile preservative free material.

The depot can be different sizes, shapes and configurations. There are several factors that can be taken into consideration in determining the size, shape and configuration of the drug depot. In addition, the shape and size of the depot should be selected so as to minimize or prevent the drug depot from moving after implantation or injection. In various embodiments, the drug depot can be shaped like a sphere, a cylinder such as a rod or fiber, a flat surface such as a disc, film, sheet, or the like. Flexibility may be a consideration so as to facilitate placement of the drug depot. In various embodiments, the drug depot can be different sizes, for example, the drug depot may be a length of from about 0.5 mm to 5 mm and have a diameter of from about 0.01 to about 2 mm. In various embodiments, the drug depot may have a layer thickness of from about 0.005 to 1.0 mm, such as, for example, from 0.05 to 0.75 mm.

Radiographic markers can be included on the drug depot or in the flowable composition to permit the user to accurately position the depot into the target site of the patient. These radiographic markers will also permit the user to track movement and degradation of the depot at the site over time. In this embodiment, the user may accurately position the depot or flowable composition in the site using any of the numerous diagnostic imaging procedures. Such diagnostic imaging procedures include, for example, X-ray imaging, MRI, or fluoroscopy. Examples of such radiographic markers include, but are not limited to, barium, calcium, and/or metal beads or particles. In various embodiments, the radiographic marker could be a spherical shape, a line(s), or a ring around the depot.

In some embodiments, the flowable composition comprises one or more biocompatible, biodegradable, and branched thermoplastic polymers, which can be made from a variety of monomers, which form polymer chains or monomeric units joined together by linking groups. These include polymers with polymer chains or backbones containing such linking groups as ester, amide, urethane, anhydride, carbonate, urea, esteramide, acetal, ketal, and orthocarbonate groups as well as any other organic functional group that can be hydrolyzed by enzymatic or hydrolytic reaction (e.g., is biodegradable by this hydrolytic action). These polymers are usually formed by reaction of starting monomers containing the reactant groups that will form these backbone linking groups. For example, alcohols and carboxylic acids will form ester linking groups. Isocyanates and amines or alcohols will respectively form urea or urethane linking groups.

Some fraction of one of these starting monomers will be multifunctional (e.g., trifunctional). This multifunctional character provides at least some branching of the resulting polymer chain. For example, when the polymer chosen contains ester linking groups along its polymer backbone, the starting monomers normally can either be hydroxycarboxylic acids or can be diols and dicarboxylic acids. The polymers can be obtained by inclusion of some fraction of a starting monomer that is at least multifunctional. In addition, the branched polymers may incorporate more than one multifunctional unit per polymer molecule, and typically many multifunctional units depending on the stoichiometry of the polymerization reaction. In some embodiments, the branched polymers incorporate at least one multifunctional unit per polymer molecule. A so-called star-branched polymer is formed when one multifunctional unit is incorporated in each polymer molecule. For example, for the ester linking group polymer described above, a dihydroxycarboxylic acid can be included with the first kind of starting monomer, or a triol and/or a tricarboxylic acid can be included with a second kind of starting monomer. Similarly, a triol, quatraol, pentaol, or hexaol such as sorbitol or glucose can be included with the first kind of starting monomer. The same rationale would apply to polyamides. A triamine and/or triacid would be included with starting monomers of a diamine and dicarboxylic acid. An amino dicarboxylic acid, diamino carboxylic acid or a triamine would be included with the second kind of starting monomer, amino acid. Any aliphatic, aromatic or arylalkyl starting monomer having the specified functional groups can be used to make the branched thermoplastic polymers, provided that the polymers and their degradation products are biocompatible. In particular, the monomers used to make the biocompatible thermoplastic branched polymers will produce polymers or copolymers that are biocompatible and biodegradable.

Examples of biocompatible, biodegradable polymers suitable for use as the biocompatible thermoplastic branched polymers of the present application include polyesters, polylactides, polyglycolides, polycaprolactones, polyanhydrides, polyamides, polyurethanes, polyesteramides, polydioxanones, polyacetals, polyketals, polycarbonates, polyorthocarbonates, polyorthoesters, polyphosphoesters, polyphosphazenes, polyhydroxybutyrates, polyhydroxyvalerates, polyalkylene oxalates, polyalkylene succinates, poly(malic acid), poly(amino acids), and copolymers, terpolymers, or combinations or mixtures of the above materials.

In some embodiments, biocompatible thermoplastic branched polymers or copolymers of the present application are those which have a lower degree of crystallization and are more hydrophobic. These polymers and copolymers are more soluble in the biocompatible organic solvents than highly crystalline polymers such as polyglycolide or chitin, which have a high degree of hydrogen-bonding. In some embodiments, the desired solubility parameters are branched polylactides, polycaprolactones, and copolymers of these with glycolide therein, where there are more amorphous regions to enhance solubility.

Generally, the biocompatible, biodegradable branched thermoplastic polymer is substantially soluble in the organic solvents so that up to 50-60 wt % solids can be made. In some embodiments, the polymers can be soluble in the organic solvent so that mixtures up to 85-98 wt % solids can be made. In some embodiments, the polymers can be insoluble in water so that less than 0.1 g of polymer per mL of water will dissolve or disperse in water. In some embodiments, the polymers used can be insoluble in water so that less than 0.001 g of polymer per mL of water will dissolve or disperse in water. At this level, the flowable composition with a completely water miscible solvent will almost immediately (e.g., within 30 minutes or less) transform to the solid or semi-solid drug depot.

Solvents suitable for use in the flowable composition are biocompatible and are at least slightly soluble in bodily fluids, tissue fluids or water. In some embodiments, the organic solvent is at soluble, moderately soluble, or very soluble, at all concentrations in bodily fluids, tissue fluids or water. A solvent that is at least slightly soluble in bodily fluids or tissue fluids to allow water to permeate into the polymer solution over a period of time ranging from seconds to weeks and cause it to coagulate or solidify. The slightly soluble solvents will slowly diffuse from the flowable composition and typically will enable the transformation to a solid or semi-solid drug depot over a period of days to weeks, e.g. about a day to several weeks. The moderately soluble to very soluble solvents will diffuse from the flowable composition over a period of minutes to days so that the transformation will occur rapidly but with sufficient leisure to allow its manipulation as a pliable implant after its placement. The highly soluble solvents will diffuse from the flowable composition over a period of seconds to hours so that the transformation will occur almost immediately. The organic solvent includes a polar aprotic or polar protic organic solvent. In some embodiments, the organic solvent may have a molecular weight in the range of about 30 to about 1000.

In some embodiments, it is believed that the transition of the flowable composition to a solid or semi-solid is the result of the dissipation of the organic solvent from the flowable composition into the surrounding aqueous medium or body fluid and the infusion of water from the surrounding aqueous medium or body fluid into the organic solvent within the flowable composition. It is also believed that during this transition, the thermoplastic polymer and organic solvent within the flowable composition partition into regions rich and poor in polymer. The regions poor in polymer become infused with water and yield the porous nature of the resulting solid or semi-solid structure.

Examples of biocompatible organic solvents that may be used to form the flowable compositions include aliphatic, aryl, and arylalkyl linear, cyclic and branched organic compounds that are liquid or at least flowable at ambient and physiological temperature and contain such functional groups as alcohols, ketones, ethers, amides, esters, carbonates, sulfoxides, sulfones, and any other functional group that is compatible with living tissue.

In some embodiments, biocompatible organic solvents that are at least slightly soluble in aqueous or body fluid include N-methyl-2-pyrrolidone, 2-pyrrolidone; C1 to C15 alcohols, diols, triols and tetraols such as ethanol, glycerine, propylene glycol, butanol; C3 to C15 alkyl ketones such as acetone, diethyl ketone or methyl ethyl ketone; C3 to C15 esters such as methyl acetate, ethyl acetate, ethyl lactate; C1 to C15 amides such as dimethylformamide, dimethylacetamide or caprolactam; C3 to C20 ethers such as tetrahydrofuran, or solketal; tweens, triacetin, propylene carbonate, decylmethylsulfoxide, dimethyl sulfoxide, oleic acid, or 1-dodecylazacycloheptan-2-one. Other solvents include, for example, benzyl alcohol, benyl benzoate, dipropylene glycol, tributyrin, ethyl oleate, glycerin, glycofural, isopropyl myristate, isopropyl palmitate, oleic acid, polyethylene glycol, propylene carbonate, dimethyl sulfoxide, triacetin, propylene carbonate or triethyl citrate. The most preferred solvents are dimethyl sulfoxide, triacetin, or propylene.

The solubility of the branched biodegradable thermoplastic polymers in the various solvents will differ depending upon their crystallinity, their hydrophilicity, hydrogen-bonding, and molecular weight. Lower molecular-weight polymers will normally dissolve more readily in the solvents than high-molecular-weight polymers. As a result, the concentration of a polymer dissolved in the various solvents will differ depending upon type of polymer and its molecular weight. Moreover, the higher molecular-weight polymers will tend to give higher solution viscosities than the low-molecular-weight materials.

Generally, the concentration of the polymer in the organic solvent can range from about 0.01 g per ml of solvent to a saturated concentration. Typically, the saturated concentration will be in the range of 80 to 95 wt % solids or 4 to almost 5 gm per ml of solvent assuming that the solvent weighs approximately 1 gm per ml.

For polymers that tend to coagulate slowly, a solvent mixture can be used to increase the coagulation rate. For example, one liquid component of the solvent mixture is a good solvent for the polymer, and the other liquid component of the solvent mixture is a poorer solvent or a non-solvent. The two liquids are mixed at a ratio such that the polymer is still soluble but precipitates with the increase in the amount of non-solvent, such as water in a physiological environment. Thus, the solvent system can be miscible with both the polymer and water. An example of such a binary solvent system is the use of N-methyl pyrrolidone and ethanol. The addition of ethanol to the NMP/polymer solution increases its coagulation rate.

Pore-Forming Additives

In some embodiments, the drug depot comprises pores in the range of from about 4 to about 1000 microns or from about 1 to about 500 microns. In some embodiments, additives can be used in controlling the pore size of the solid drug depot, which influences the structure of the depot and the release rate of the therapeutic agent and/or the diffusion rate of body fluids. For example, if the flowable composition is too impervious to bodily fluids medium, water or tissue ingrowth, a pore-forming agent can be added to generate additional pores in the drug depot. Any biocompatible water-soluble material can be used as the pore-forming additive. These additives can be either soluble in the flowable composition or simply dispersed within it. They are capable of dissolving, diffusing or dispersing out of both the coagulating polymer matrix whereupon pores and microporous channels are generated. The amount of pore-forming additive (and size of dispersed particles of such pore-forming agent, if appropriate) within the flowable composition will directly affect the size and number of the pores in the polymer matrix of the drug depot.

Pore-forming additives include any pharmaceutically acceptable organic or inorganic substance that is substantially miscible in water and body fluids and will dissipate from the forming and formed matrix into aqueous medium or body fluids or water-immiscible substances that rapidly degrade to water soluble substances. In some embodiments, the pore-forming additive is miscible or dispersible in the organic solvent to form a uniform mixture. Suitable pore-forming agents include, for example, sugars such as sucrose or dextrose, salts such as sodium chloride or sodium carbonate, and polymers such as hydroxylpropylcellulose, carboxymethylcellulose, polyethylene glycol, or polyvinylpyrrolidone. The size and extent of the pores can be varied over a wide range by changing the molecular weight and percentage of pore-forming additive incorporated into the flowable composition.

Upon contact with bodily fluid, the solvent and optional pore-forming additive dissipate into surrounding tissue fluids. This causes the formation of microporous channels within the coagulating polymer matrix. Optionally, the pore-forming additive may dissipate from the matrix into the surrounding tissue fluids at a rate slower than that of the solvent, or be released from the matrix over time by biodegradation or bioerosion of the matrix. In some embodiments, the pore-forming additive dissipates from the coagulating implant matrix within a short time following implantation such that a matrix is formed with a porosity and pore structure effective to sustain release the drug over the desired period of time.

Porosity of the solid polymer matrix may be varied by the concentration of water-soluble or water-miscible ingredients, such as the solvent and/or pore-forming agent, in the polymer composition. For example, a high concentration of water-soluble substances in the thermoplastic composition may produce a polymer matrix having a high degree of porosity. The concentration of the pore-forming agent relative to polymer in the composition may be varied to achieve different degrees of pore-formation, or porosity, in the drug depot matrix. Generally, the polymer composition will include about 0.01-1 gram of pore-forming agent per gram polymer.

The size or diameter of the pores formed in the matrix of the solid implant may be modified according to the size and/or distribution of the pore-forming agent within the polymer matrix. For example, pore-forming agents that are relatively insoluble in the polymer mixture may be selectively included in the polymer composition according to particle size in order to generate pores having a diameter that corresponds to the size of the pore-forming agent. Pore-forming agents that are soluble in the polymer mixture may be used to vary the pore size and porosity of the implant matrix by the pattern of distribution and/or aggregation of the pore-forming agent within the polymer mixture and coagulating and solid polymer matrix.

In some embodiments, after the flowable composition solidifies, the drug depot can have pore diameters of about 3 to about 500 microns or about 5 to about 250 microns and a porosity of about 5-95% or 25-85% in order to provide drug release.

Solvent Depletion Depot

In some embodiments, the depot is administered as a liquid and then sets or cures into a gel or solid within the patient's body as a solvent diffuses away or dissipates from the depot. This type of depot is referred to as a "solvent-depletion depot".

For solvent-depletion depots, one can use any number of polymers to make the depot including, but not limited to, polylactides, polyglycolides, polycaprolactones, polyanhydrides, polyamines, polyurethanes, polyesteramides, polyorthoesters, polydioxanones, polyacetals, polyketals, polycarbonates, polyorthocarbonates, polyphosphazenes, succinates, poly(malic acids), poly(amino acids), polyvinylpyrrolidone, polyethylene glycol, polyhydroxycellulose, chitin, chitosan, and copolymers, terpolymers, or mixtures thereof.

In some embodiments, one may want to make the depots using polymers with a lower degree of crystallization and which are more hydrophobic. Examples of such polymers are polylactides, polycaprolactones, and copolymers of these with glycolide therein which there are more amorphous regions to enhance solubility.

The solvent used in these solvent-depletion depots should be non-toxic at the levels used in the composition. In some embodiments, the solvents are water miscible. The solvents can include, but are not limited to, triacetin, N-methyl-2-pyrrolidone, 2-pyrrolidone, ethanol, glycerol formal, propylene glycol, acetone, methyl acetate, benzyl benzoate, benzyl alcohol, ethyl acetate, methyl ethyl ketone, dimethylformamide, dimethyl sulfoxide, tetrahydrofuran, caprolactam, decylmethylsulfoxide, oleic acid, 1-dodecylazacyclo-heptan-2-one, or mixtures thereof.

The solvent-depletion depot can optionally have one or more emulsifying agents. Examples of emulsifying agents include, but are not limited to, water, ethanol, other alcohols, polyols, esters, carboxylic acids, ketones, aldehydes, propylene glycol, ethylene glycol, glycerol, and solutions and mixtures thereof.

The proportions of a solvent-depletion depot can range as follows, expressed as a percentage of the total weight of the composition prior to administration to a subject:
Polymer about 5% to about 90%
Solvent about 15% to about 95%
Emulsifying about 0% to about 80%
Pharmaceutical agent about 0.1% to about 50%
Diluents about 0% to about 40%

If the therapeutic agent is hydrophilic, then one may want to use polar solvents (albeit a polar solvent that is not toxic to the subject in the levels used). Polar solvents should be somewhat water soluble, having a Hildebrand Solubility Parameter of at least about 7.5 or 8 $(cal/cc)^{1/2}$, usually at least about 9 $(cal/cc)^{1/2}$, and often times, 10 $(cal/cc)^{1/2}$.

The solvent depletion depot may also have one or more pore-forming additives as discussed above.

Thermosetting Depot

In some embodiments, the polymer within the depot can be thermosetting, e.g., it changes from a liquid at room temperature to a solid or gel at body temperature when the liquid reaches a pre-determined temperature. This type of depot is referred to as a "thermosetting depot". The sol-to-gel transition temperature can be above room temperature (e.g., 64.4° F.-75.2° F.) to body temperature (e.g., 96° F.-105° F.).

Thermosetting depots typically involve a mixture of polymers that form a block copolymer having hydrophobic segments and hydrophilic segments. A block copolymer can be a tripolymer of hydrophobic-hydrophilic-hydrophobic segments or hydrophilic-hydrophobic-hydrophilic segments. Alternatively, the block copolymer can be a repeating hydrophobic-hydrophilic or hydrophilic-hydrophobic segments with one additional segment.

The hydrophobic polymers can include, but are limited to, poly(D,L-lactic acid), poly(L-lactic acid), poly(D-lactic acid), poly(D,L-lactic-co-glycolic acid), poly(L-lactic-co-glycolic acid), poly(ε-caprolactone), poly(γ-butyrolactone), poly(δ-valerolactone), poly(ε-caprolactone-co-lactic acid), poly(ε-caprolactone-co-glycolic acid-co-lactic acid), hydroxybutyric acid, malic acid, and bi- or terpolymers thereof. Another hydrophobic polymer can be poly(ethylene carbonate). In some embodiments the average molecular weight of the hydrophobic polymer blocks are less than 100,000. The average molecular in other embodiments can range from about 1,000 to about 3,000 or from about 1,000 to about 10,000.

The hydrophilic polymer can include, but is not limited to, polyethylene glycol, and polyethylene oxides. In some embodiments, the above molecular weight of the hydrophilic polymer blocks are between 300 and 20,000. In other embodiments, the average molecular weight is between about 500 and 10,000.

Other examples of thermosetting depots can contain block polymers of polyethylene oxides (as known as polyoxyethylene or PEO) and poly-propylene oxide (also known as polyoxypropylene or PPO) (PEO-PPO-PEO, Pluronics®, BASF, Florham Park, N.J.); block polymers of polyethylene oxides, poly-propylene oxide, and poly(aspartic acid) (PEO-PPO-PAA); and poly(lactide-co-glycolide) or block polymers of polyethylene oxides (PLGA-PEO-PLGA).

For thermosetting depots, the amount of polymer in the depot can range from about 1% to about 99% by weight, the pharmaceutical agent can range from about 0.1% to about 50% by weight, and the diluents can range from 0% to about 60% by weight.

In various embodiments, the flowable composition and/or drug depot may comprise poly (alpha-hydroxy acids), poly (lactide-co-glycolide) (PLGA), polylactide (PLA), polyglycolide (PG), polyethylene glycol (PEG) conjugates of poly (alpha-hydroxy acids), polyorthoesters, polyaspirins, polyphosphagenes, collagen, starch, pre-gelatinized starch, hyaluronic acid, chitosans, gelatin, alginates, albumin, fibrin, vitamin E analogs, such as alpha tocopheryl acetate, d-alpha tocopheryl succinate, D,L-lactide, or L-lactide, -caprolactone, dextrans, vinylpyrrolidone, polyvinyl alcohol (PVA), PVA-g-PLGA, PEGT-PBT copolymer (polyactive), methacrylates, poly (N-isopropylacrylamide), PEO-PPO-PEO (pluronics), PEO-PPO-PAA copolymers, PLGA-PEO-PLGA, PEG-PLG (poly(d,l-lactide-co-glycolide), PLA-PLGA, poloxamer 407, PEG-PLGA-PEG triblock copolymers, SAIB (sucrose acetate isobutyrate) or combinations thereof. These one or more components allow the therapeutic agent to be released from the composition in a controlled and/or sustained manner. For example, the flowable composition containing the therapeutic agent and a polymer matrix can be injected at the target tissue site and the polymer matrix breaks down over time (e.g., days, months) within the target tissue site releasing the therapeutic agent. The depot is capable of carrying at least one pharmaceutical agent in quantities sufficient for therapeutic or prophylactic treatment over a pre-selected period of time. The depot can release the therapeutic agent over 1 day, over 2 days, over 3 days, over 4 days, over 5 days, over 10 days, over 15 days, over 20 days, or over 30 days. In an alternative embodiment, the depot can release the therapeutic agent over 30 days, over 60 days, over 90 days, over 180 days, over 6 months, over 9 months, over 12 months, over 14 months, over 16 months, and over 18 months. In another embodiment, the depot can contain two or more therapeutic agents, each one being released over different number of days or months.

The terms "sustained release" (e.g., extended release or controlled release) are used herein to refer to one or more therapeutic agent(s) that is introduced into the body of a human or other mammal and continuously releases a stream of one or more therapeutic agents over a predetermined time period and at a therapeutic level sufficient to achieve a desired therapeutic effect throughout the predetermined time period. Reference to a continuous release stream is intended to encompass release that occurs as the result of biodegradation in vivo of the drug depot, or a matrix or component thereof, or as the result of metabolic transformation or dissolution of the therapeutic agent(s) or conjugates of therapeutic agent(s).

In various embodiments, the flowable composition and/or drug depot can be designed to cause an initial burst dose of therapeutic agent within the first 24 hours after implantation. "Initial burst" or "burst effect" or "bolus dose" refers to the release of therapeutic agent from the flowable composition and/or depot during the first 24 hours after the flowable composition and/or drug depot comes in contact with an aqueous fluid (e.g., synovial fluid, cerebral spinal fluid, etc.). The "burst effect" could be due to the increased release of therapeutic agent from the flowable composition and/or depot while it is coagulating or hardening to form a solid or semi solid (rubbery) implant. In alternative embodiments, the flowable composition and/or depot is designed to avoid this initial burst effect.

In various embodiments, the flowable composition has a pre-dosed viscosity in the range of about 1 to about 500 centipoise (cps), 1 to about 200 cps, or 1 to about 100 cps. After the flowable composition is administered to the target site, the viscosity of the flowable composition will increase and the flowable composition will have a modulus of elasticity (Young's modulus) in the range of about $1 \times 10^4$ to about $6 \times 10^5$ dynes/cm$^2$, or $2 \times 10^4$ to about $5 \times 10^5$ dynes/cm$^2$, or $5 \times 10^4$ to about $5 \times 10^5$ dynes/cm$^2$.

In various embodiments, flowable composition is provided that hardens or stiffens after delivery. Typically, hardening formulations may have a pre-dosed modulus of elasticity in the range of about $1 \times 10^4$ to about $3 \times 10^5$ dynes/cm$^2$, or $2 \times 10^4$ to about $2 \times 10^5$ dynes/cm$^2$, or $5 \times 10^4$ to about $1 \times 10^5$ dynes/cm$^2$. The post-dosed hardening formulation (after delivery) may have a rubbery consistency and have a modulus of elasticity in the range of about $1 \times 10^4$ to about $2 \times 10^6$ dynes/cm$^2$, or $1 \times 10^5$ to about $7 \times 10^5$ dynes/cm$^2$, or $2 \times 10^5$ to about $5 \times 10^5$ dynes/cm$^2$.

In various embodiments, for those flowable compositions that contain a polymer, the polymer concentration may affect the rate at which the composition hardens (e.g., a gel with a higher concentration of polymer may coagulate more quickly than compositions having a lower concentration of polymer). In various embodiments, when the composition hardens, the resulting matrix is solid but is also able to conform to the irregular surface of the tissue (e.g., recesses and/or projections in bone).

The percentage of polymer present in the flowable composition may also affect the viscosity of the flowable composition. For example, a composition having a higher percentage by weight of polymer is typically thicker and more viscous than a composition having a lower percentage by weight of polymer. A more viscous composition tends to flow more slowly. Therefore, a composition having a lower viscosity may be preferred in some instances, for example, when applying the formulation via spray.

In various embodiments, the molecular weight of the flowable composition can be varied by many methods known in the art. The choice of method to vary molecular weight is typically determined by the type of flowable composition to be used (e.g., polymer, versus non-polymer). For example in various embodiments, when the flowable composition comprises one or more polymers, the degree of polymerization can be controlled by varying the amount of polymer initiators (e.g. benzoyl peroxide), organic solvents or activator (e.g. DMPT), crosslinking agents, emulsifying agents, polymerization agent, and/or reaction time.

When the composition is designed to be a flowable composition, it can vary from low viscosity, similar to that of water, to a high viscosity, similar to that of a paste, depending on the molecular weight and concentration of the polymer used in the flowable composition. The viscosity of the flowable composition can be varied such that the polymeric composition can be applied to a patient's tissues by any convenient technique, for example, by brushing, spraying, dripping, injecting, or painting. Different viscosities of the flowable composition will depend on the technique used to apply the composition. For example, spraying requires a flowable composition having a low viscosity.

In various embodiments, the flowable composition has an inherent viscosity (abbreviated as "I.V." and units are in deciliters/gram), which is a measure of the flowable composition's molecular weight and degradation time (e.g., a flowable composition with a high inherent viscosity has a higher molecular weight and longer degradation time). Typically, a flowable composition with a high molecular weight provides a stronger matrix and the matrix takes more time to degrade. In contrast, a flowable composition with a low molecular weight degrades more quickly and provides a softer matrix. In various embodiments, the flowable composition has a molecular weight, as shown by the inherent viscosity, from about 0.10 dL/g to about 1.2 dL/g or from about 0.10 dL/g to about 0.40 dL/g.

Gel

In one exemplary embodiment, the flowable composition is a gel for delivering a therapeutic agent to a target tissue site beneath the skin of a patient. The gel being capable of solidifying or hardening at the target tissue site, wherein the target tissue site comprises at least one muscle, ligament, tendon, cartilage, spinal disc, spinal foraminal space near the spinal nerve root, facet or synovial joint, or spinal canal. In various embodiments, the gel includes a substance having a gelatinous, jelly-like, or colloidal properties at room temperature. The gel, in various embodiments, may have the therapeutic agent dispersed throughout it or one or more drug depots comprising the therapeutic agent may be suspended within the gel. The dispersal of the therapeutic agent may be even throughout the gel. Alternatively, the concentration of the therapeutic agent may vary throughout it. As the biodegradable material of the gel or drug depot degrades at the site, the therapeutic agent is released.

In another exemplary embodiment, the gel in viscous form is loaded with one or more drug depots (e.g., microspheres loaded with a therapeutic agent), wherein the viscous gel is positioned into a synovial joint, disc space, a spinal canal, or a soft tissue surrounding the spinal canal of a subject. In yet another exemplary embodiment, the gel is a sprayable, injectable, and/or an adherent gel that solidifies upon contact with tissue. For example, the gel may be administered as a liquid that gels in situ at the target tissue site. In various embodiments, the gel can comprise a two part system where a liquid is administered and a gelling agent is added subsequently to cause the liquid to gel or harden.

In various embodiments, the gel is a hardening gel, which is separate from the drug depot and applied before, during or after implantation of the drug depot. After the gel is applied to the target site, it hardens holding the drug depot in place in this way the need to suture the depot to the target tissue site is avoided.

In various embodiments, the gel is a viscous gel loaded with a drug depot, which delivers the therapeutic agent to the desired target tissue site (e.g., inflamed tissue, degenerative tissue, etc.). The viscous gel then hardens and prevents the drug depot from being removed from that site by the venous systemic circulation or otherwise dispersed too widely, which reduces the desired therapeutic effect. For example, after hours or days, the gel may be absorbed, thereby allowing the drug depots (e.g., microspheres) to begin releasing the therapeutic agent. The microspheres may not begin releasing the agent until they are released from the gel. So, the microspheres may be formed from an insoluble or inert substance that becomes soluble or active once it comes into contact with the target tissue site. Likewise, the gel may comprise a substance that dissolves or disperses within the tissue. As the gel begins to dissolve within hours to days, the drug depots (e.g., microspheres) are exposed to body fluids and begin releasing their contents. So, the gel may comprise the same or different material as the drug depot (e.g., POE, PEG). The gel and drug depot can be formulated to optimize exposure time of the drug depot and release of the therapeutic agent from the drug depot.

In one embodiment, a depot is provided that comprises an adherent gel comprising a therapeutic agent that is evenly distributed throughout the gel. The gel may be of any suitable type, as previously indicated, and should be sufficiently viscous so as to prevent the gel from migrating from the targeted tissue site once deployed; the gel should, in effect, "stick" or adhere to the targeted tissue site. The gel may, for example, solidify upon contact with the targeted tissue or after deployment from a targeted delivery system. The targeted delivery system may be, for example, a syringe, a catheter, needle or cannula or any other suitable device. The targeted delivery system may inject or spray the gel into or on the targeted tissue site. The therapeutic agent may be mixed into the gel prior to the gel being deployed at the targeted tissue site. In various embodiments, the gel may be part of a two-component delivery system and when the two components are mixed, a chemical process is activated to form the gel and cause it to stick or adhere to the target tissue. In various embodiments, the gel may also adhere to the targeted tissue site by a mechanical interdigitation with the target tissue prior to hardening. In other embodiments, the gel may adhere to the target tissue site by chemical bonding of the gel to the target tissue site (e.g., ionic bonding, covalent bonding, hydrogen bonding, electrostatic interaction, hydrophobic, hydrophilic or other interaction with target tissue site). In still other embodiments, the gel may adhere to the target tissue site by a combination of chemical bonding and mechanical interdigitation.

In various embodiments, the gel can have a viscosity of about 300 to about 5,000 centipoise (cp). In other embodiments, the gel can have a viscosity of from about 5 to about 300 cps, from about 10 cps to about 50 cps, from about 15 cps to about 75 cps at room temperature, which allows it to be sprayed at or near the target site. The gel may optionally have a viscosity enhancing agent such as, for example, hydroxypropyl cellulose, hydroxypropyl methylcellulose, hydroxyethyl methylcellulose, carboxymethylcellulose and salts thereof, Carbopol, poly(hydroxyethylmethacrylate), poly(methoxyethylmethacrylate), poly(methoxyethoxyethyl methacrylate), polymethylmethacrylate (PMMA), methylmethacrylate (MMA), gelatin, polyvinyl alcohols, propylene glycol, PEG 200, PEG 300, PEG 400, PEG 500, PEG 600, PEG 700, PEG 800, PEG 900, PEG 1000, PEG 1450, PEG 3350, PEG 4500, PEG 8000 or combinations thereof.

The sprayability of the gel can be controlled, among other things, by controlling the particle size distribution of the gel components. In various embodiments, the particle size distribution of the depots suspended in the gel may be in the range of from about 10 μm to 100 μm so that the gel can easily be sprayed at or near the target site.

In contrast, to a sprayable gel that typically employs a low viscosity polymer, a gel with a higher viscosity may be desirable for other applications, for example, a gel having a putty-like consistency may be more preferable for bone regeneration applications. In various embodiments, when a polymer is employed in the gel, the polymeric composition includes about 10 wt % to about 90 wt % or about 30 wt % to about 60 wt % of the polymer.

In various embodiments, the gel is a hydrogel made of high molecular weight biocompatible elastomeric polymers of synthetic or natural origin. A desirable property for the hydrogel to have is the ability to respond rapidly to mechanical stresses, particularly shears and loads, in the human body.

Hydrogels obtained from natural sources are particularly appealing since they are more likely to be biodegradable and biocompatible for in vivo applications. Suitable hydrogels include natural hydrogels, such as for example, gelatin, collagen, silk, elastin, fibrin and polysaccharide-derived polymers like agarose, and chitosan, glucomannan gel, hyaluronic acid, polysaccharides, such as cross-linked carboxyl-containing polysaccharides, or a combination thereof. Synthetic hydrogels include, but are not limited to those formed from polyvinyl alcohol, acrylamides such as polyacrylic acid and poly (acrylonitrile-acrylic acid), polyurethanes, polyethylene glycol (e.g., PEG 3350, PEG 4500, PEG 8000), silicone, polyolefins such as polyisobutylene and polyisoprene, copolymers of silicone and polyurethane, neoprene, nitrile, vulcanized rubber, poly(N-vinyl-2-pyrrolidone), acrylates such as poly(2-hydroxy ethyl methacrylate) and copolymers of acrylates with N-vinyl pyrrolidone, N-vinyl lactams, polyacrylonitrile or combinations thereof. The hydrogel materials may further be cross-linked to provide further strength as needed. Examples of different types of polyurethanes include thermoplastic or thermoset polyurethanes, aliphatic or aromatic polyurethanes, polyetherurethane, polycarbonate-urethane or silicone polyether-urethane, or a combination thereof.

In various embodiments, rather than directly admixing the therapeutic agent into the gel, microspheres may be dispersed within the gel, the microspheres loaded with the therapeutic agent. In one embodiment, the microspheres provide for a sustained release of the therapeutic agent. In yet another embodiment, the gel, which is biodegradable, prevents the microspheres from releasing the therapeutic agent; the microspheres thus do not release the therapeutic agent until they have been released from the gel. For example, a gel may be deployed around a target tissue site (e.g., a nerve root). Dispersed within the gel are a plurality of microspheres that encapsulate the desired therapeutic agent. Certain of these microspheres degrade once released from the gel, thus releasing the therapeutic agent.

Microspheres, much like a fluid, may disperse relatively quickly, depending upon the surrounding tissue type, and hence disperse the therapeutic agent. In some situations, this may be desirable; in others, it may be more desirable to keep the therapeutic agent tightly constrained to a well-defined target site. The present application also contemplates the use of adherent gels to constrain dispersal of the therapeutic agent. These gels may be deployed, for example, in a disc space, in a spinal canal, or in surrounding tissue, or in a joint space, such as a synovial cavity. In this embodiment the gel is an adherent and/or settable gel that stays in place within a joint space.

Cannula or Needle

It will be appreciated by those with skill in the art that the flowable composition can be administered to the target site using a cannula or needle that can be a part of a drug delivery device e.g., a syringe, a gun drug delivery device, or any medical device suitable for the application of a drug to a targeted organ or anatomic region. The cannula or needle of the drug depot device is designed to cause minimal physical and psychological trauma to the patient.

Cannulas or needles include tubes that may be made from materials, such as for example, polyurethane, polyurea, polyether(amide), PEBA, thermoplastic elastomeric olefin, copolyester, and styrenic thermoplastic elastomer, steel, aluminum, stainless steel, titanium, metal alloys with high non-ferrous metal content and a low relative proportion of iron, carbon fiber, glass fiber, plastics, ceramics or combinations thereof. The cannula or needle may optionally include one or more tapered regions. In various embodiments, the cannula or needle may be beveled. The cannula or needle may also have a tip style vital for accurate treatment of the patient depending on the site for implantation. Examples of tip styles include, for example, Trephine, Coumand, Veress, Huber, Seldinger, Chiba, Francine, Bias, Crawford, deflected tips, Hustead, Lancet, or Tuohey. In various embodiments, the cannula or needle may also be non-coring and have a sheath covering it to avoid unwanted needle sticks.

The dimensions of the hollow cannula or needle, among other things, will depend on the site for implantation. For example, the width of the epidural space is only about 3-5 mm for the thoracic region and about 5-7 mm for the lumbar region. Thus, the needle or cannula, in various embodiments, can be designed for these specific areas. In various embodiments, the cannula or needle may be inserted using a transforaminal approach in the spinal foramen space, for example, along an inflammed nerve root and the drug depot implanted at this site for treating the condition. Typically, the transforaminal approach involves approaching the intervertebral space through the intervertebral foramina.

Some examples of lengths of the cannula or needle may include, but are not limited to, from about 50 to 150 mm in length, for example, about 65 mm for epidural pediatric use, about 85 mm for a standard adult and about 110 mm for an obese adult patient. The thickness of the cannula or needle will also depend on the site of implantation. In various embodiments, the thickness includes, but is not limited to, from about 0.05 to about 1.655. The gauge of the cannula or needle may be the widest or smallest diameter or a diameter in between for insertion into a human or animal body. The widest diameter is typically about 14 gauge, while the smallest diameter is about 22 gauge. In various embodiments the gauge of the needle or cannula is about 18 to about 22 gauge.

In various embodiments, like the drug depot and/or gel, the cannula or needle includes dose radiographic markers that indicate location at or near the site beneath the skin, so that the user may accurately position the depot at or near the site using any of the numerous diagnostic imaging procedures. Such diagnostic imaging procedures include, for example, X-ray imaging, MRI, or fluoroscopy. Examples of such radiographic markers include, but are not limited to, barium, calcium phosphate, and/or metal beads or particles.

In various embodiments, the needle or cannula may include a transparent or translucent portion that can be visualizable by ultrasound, fluoroscopy, x-ray, or other imaging techniques. In such embodiments, the transparent or translucent portion may include a radiopaque material or ultrasound responsive topography that increases the contrast of the needle or cannula relative to the absence of the material or topography.

The flowable composition and/or medical device to administer the drug may be sterilizable. In various embodiments, one or more components of the flowable composition and/or medical device to administer the drug are sterilized by radiation in a terminal sterilization step in the final packaging. Terminal sterilization of a product provides greater assurance of sterility than from processes such as an aseptic process, which require individual product components to be sterilized separately and the final package assembled in a sterile environment.

Typically, in various embodiments, gamma radiation is used in the terminal sterilization step, which involves utilizing ionizing energy from gamma rays that penetrates deeply in the device. Gamma rays are highly effective in killing microorganisms, they leave no residues nor have sufficient energy to impart radioactivity to the device. Gamma rays can be employed when the device is in the package and gamma sterilization does not require high pressures or vacuum conditions, thus, package seals and other components are not stressed. In addition, gamma radiation eliminates the need for permeable packaging materials.

In various embodiments, electron beam (e-beam) radiation may be used to sterilize one or more components of the device. E-beam radiation comprises a form of ionizing energy, which is generally characterized by low penetration and high-dose rates. E-beam irradiation is similar to gamma processing in that it alters various chemical and molecular bonds on contact, including the reproductive cells of microorganisms. Beams produced for e-beam sterilization are concentrated, highly-charged streams of electrons generated by the acceleration and conversion of electricity. E-beam sterilization may be used, for example, when the flowable composition is a gel that contains one or more drug depots disposed within the gel.

Other methods may also be used to sterilize the flowable composition and/or one or more components of the device, including, but not limited to, gas sterilization, such as, for example, with ethylene oxide or steam sterilization.

In various embodiments, a kit is provided which may include additional parts along with the flowable composition, drug depot and/or medical device combined together to be used to implant the flowable composition and/or drug depot. The kit may include the drug depot device in a first compartment. The second compartment may include a canister holding the flowable composition to be sprayed at the target site, and any other instruments needed for the localized drug delivery. A third compartment may include gloves, drapes, wound dressings and other procedural supplies for maintaining sterility of the implanting process, as well as an instruction booklet. A fourth compartment may include additional cannulas and/or needles. Each tool may be packaged together or separately in a plastic pouch that is radiation sterilized. A cover of the kit may include illustrations of the implanting procedure and a clear plastic cover may be placed over the compartments to maintain sterility.

In some embodiments, the kit comprising the flowable composition is packaged in a moisture resistant package that is terminally sterilized. So the user just opens one package. In some embodiments, a kit is provided for implanting a drug depot at or near a target tissue site beneath the skin of a patient, the kit comprising (i) an implantable drug depot having a chamber disposed within the drug depot; and (ii) a flowable composition comprising an effective amount of a therapeutic agent, the flowable composition capable of hardening inside the chamber of the drug depot when the drug depot is implanted at or near the target tissue site; wherein the drug depot is capable of releasing the therapeutic agent over a period of at least one day.

Drug Delivery

In various embodiments, it is advantageous to have a depot that does not require highly invasive delivery techniques. Rather, having a depot that can be injected using a syringe and needle into the joint or into tissue adjacent to the joint is beneficial to recover from the injury or disease within the joint. It is worth noting, however, that the present application can also be delivered using minimally invasive surgical or open surgical procedures.

In various embodiments, a method for delivering a therapeutic agent into a synovial joint of a patient is provided, the method comprising inserting a cannula at or near a target tissue site in the synovial joint and implanting the drug depot at the target site beneath the skin of the patient and brushing, spraying, dripping, injecting, or painting the gel in the target site to hold or have the drug depot adhere to the target site. In this way unwanted migration of the drug depot away from the target site is reduced or eliminated.

In various embodiments, to administer the flowable composition having the drug depot dispersed therein to the desired site, first the cannula or needle can be inserted through the skin and soft tissue down to the target tissue site and the flowable composition administered (e.g., brushed, sprayed, dripped, injected, or painted, etc.) at or near the target site. In some embodiments where the drug depot is separate from the flowable composition (such as where the drug depot contains a confining element such as a chamber), first the cannula or needle can be inserted through the skin and soft tissue down to the site of injection and the drug depot deployed. Following administration of the drug depot, the flowable composition can be used to fill the drug depot chamber. In this way, the drug depot will expand on filling and/or as the flowable composition hardens so that the drug depot can be held in place or reduced migration of the drug depot. Alternatively, the drug depot may be implanted first and then the flowable composition placed (e.g., brushed, sprayed, dripped, injected, or painted, etc.) around the drug depot to hold it in place. By using the flowable composition, accurate and precise implantation of a drug depot can be accomplished with minimal physical and psychological trauma to the patient. The flowable composition avoids the need to suture the drug depot to the target site reducing physical and psychological trauma to the patient.

In various embodiments, when the target site comprises a joint or spinal region, a portion of fluid (e.g., synovial fluid, spinal fluid, etc.) can be withdrawn from the target site through the cannula or needle first and then the flowable composition administered (e.g., brushed, sprayed, dripped, injected, or painted, etc.) where it will harden. The target site will re-hydrate (e.g., replenishment of fluid) and this aqueous environment will cause the drug to be released from the depot.

The flowable composition may be used for localized delivery of the therapeutic agent to the patient to treat a disease or condition such as for example, osteoarthritis, rheumatoid arthritis, sciatica, carpal tunnel syndrome, lower back pain, lower extremity pain, upper extremity pain, cancer, tissue pain and pain associated with injury or repair of cervical, thoracic, and/or lumbar vertebrae or intervertebral discs, rotator cuff, articular joint, TMJ, tendons, ligaments, muscles, or the like. In various embodiments, the flowable composition may also be used to repair tissue as well deliver a therapeutic agent.

Patients include a biological system to which a treatment can be administered. A biological system can include, for example, an individual cell, a set of cells (e.g., a cell culture), an organ, or a tissue. Additionally, the term "patient" can refer to animals, including, without limitation, humans.

Treating or treatment of a disease refers to executing a protocol, which may include administering one or more drugs to a patient (human or otherwise), in an effort to alleviate signs or symptoms of the disease. Alleviation can occur prior to signs or symptoms of the disease appearing, as well as after their appearance. Thus, "treating" or "treatment" includes "preventing" or "prevention" of disease. In addition, "treating" or "treatment" does not require complete alleviation of signs or symptoms, does not require a cure, and specifically includes protocols that have only a marginal effect on the patient.

"Localized" delivery includes, delivery where one or more drugs are deposited within a tissue, for example, a nerve root of the nervous system or a region of the brain, or in close proximity (within about 10 cm, or preferably within about 5 cm, for example) thereto. "Targeted delivery system" provides delivery of the flowable composition and/or depot at or near the target site as needed for treatment of pain, inflammation or other disease or condition.

In various embodiments, the flowable composition may be used to treat rheumatoid arthritis (RA) and/or osteoarthritis by inserting a cannula at or near a target tissue site by brushing, spraying, dripping, injecting, or painting the flowable composition at the target site and allowing it to harden into the drug depot.

RA is a chronic systemic disease characterized by progressive joint deformity and joint destruction in which cytokines play a central pathogenic role. The clinical course of RA is variable and often shows a remitting pattern. Three forms of RA can be distinguished: mild, self-limiting disease; mildly progressive disease; and aggressive disease, which is difficult to control with medication, and is characterized by functional decline and radiologic deterioration of the joints, e.g., joint space narrowing and erosions. In accordance with the systemic nature of RA, there are extra-articular manifestations, which include vasculitis, alveolitis, and ocular disease. Onset of RA is often insidious with fatigue, anorexia, generalized weakness, and vague musculoskeletal symptoms. Specific symptoms appear later. Several joints, usually in a symmetrical fashion, are affected. Most often these are joints of the hands, wrists, knees, and feet. Joints are painful and swollen, and motion is limited. With persistent inflammation, a variety of deformities develop which include most typically radial deviation of the wrist and hyperextension or flexion of the proximal interphalangeal joints; other deformities occur as well. Atrophy of skeletal muscle sets in. In approximately 20 to 30% of all patients, there is development of rheumatoid nodules on periarticular structures or sites of trauma, but they are usually of limited clinical significance. The nodules may be found in other structures such as the pleura or the meninges. Laboratory findings may include elevation of erythrocyte sedimentation rate (ESR) and C-reactive protein (CRP) along with rheumatoid factor. Rheumatoid factor is an autoantibody against the Fc portion of IgG found in more than two-thirds of all patients. High titers of rheumatoid factor are a good indicator of disease activity. Mild anemia (normochromic, normocytic) and eosinophilia may be present as well. With progression of the disease, X-ray abnormalities such as general deformity, juxta-articular osteopenia, loss of articular cartilage, and bone erosion become more evident.

In one exemplary embodiment, the flowable composition is utilized to treat osteoarthritis (OA), which is the most common form of arthritis in Western populations. Knee OA, characterized clinically by pain and functional disability, is the leading cause of chronic disability among the elderly in the US. Risk factors for OA include age, gender, race, trauma, repetitive stress/joint overload, muscle weakness, and genetic factors. Pathologically, the most striking changes in OA are focal loss of articular cartilage and marginal and central new bone formation. However, OA is not simply a disease of articular cartilage and the subchondral bone. Rather, it is a disease of the synovial joint, with alterations also found in the synovium, capsule, ligaments, periarticular muscle, and sensory nerves.

Although OA was once considered a non-inflammatory arthropathy, patients often present with signs and symptoms consistent with local inflammation and synovitis, and inflammation and inflammatory mediators play a role in the joint destruction associated with OA as well as in pain. Both chondrocytes and synovium in OA can produce proinflammatory cytokines, including IL-1β, which can alter cartilage homeostasis in favor of cartilage degradation. For example, IL-1β appears to be a major factor stimulating matrix metalloproteinase synthesis and other cartilage catabolic responses in OA.

FIG. 1 illustrates one embodiment of the effect of osteoarthritis on the joint 10. Osteoarthritis causes the cartilage 13 to become worn away from the ends of the bones 11, 12. Fragments of cartilage may break off from the bones and become suspended in the synovial fluid 16. Bone spurs (20 in FIG. 2) may grow out from the edge of the bones 11 and 12. Osteoarthritis may also cause the synovial membrane 15 that produces a synovial fluid 16 to nourish and lubricate the cartilage 13 to produce an increased amount of synovial fluid 16. Altogether, the joint 10 may become swollen and/or feel stiff and sore. Muscles 17, connective tendons 18, and other tissue (e.g., ligaments) surround the joint capsule 14 and keep the bones 11, 12 stable and allow the joint 10 to bend and move. However, symptoms become worse and debilitating as the disease progresses. To treat the diseased joint, the flowable composition 22 can be administered locally at the target site utilizing a cannula or needle 24 that penetrates beneath the skin to the target site 22. In this embodiment, the flowable composition contains the depot suspended in it and the flowable composition is sprayed at the target site (shown at or near the osteolytic lesions). It will be understood that some synovial fluid 16 may be withdrawn from the joint 10 and the flowable composition added before, during, or after the synovial fluid is withdrawn so that as the joint re-hydrates, the therapeutic agent will be released as the fluid contacts the drug depot. The flowable composition may also be placed at other target sites (e.g., by the meniscus or cartilage surface) and the drug released. In this way, accurate and precise implantation of a drug depot in a minimally invasive procedure can be accomplished. In various embodiments, the flowable composition avoids the need to suture the drug depot to the target site reducing physical and psychological trauma to the patient. In various embodiments, when several drug depots are to be implanted, the flowable composition allows accurate placement of the drug depot in a manner to optimize location, accurate spacing, and drug distribution.

Figure 2:
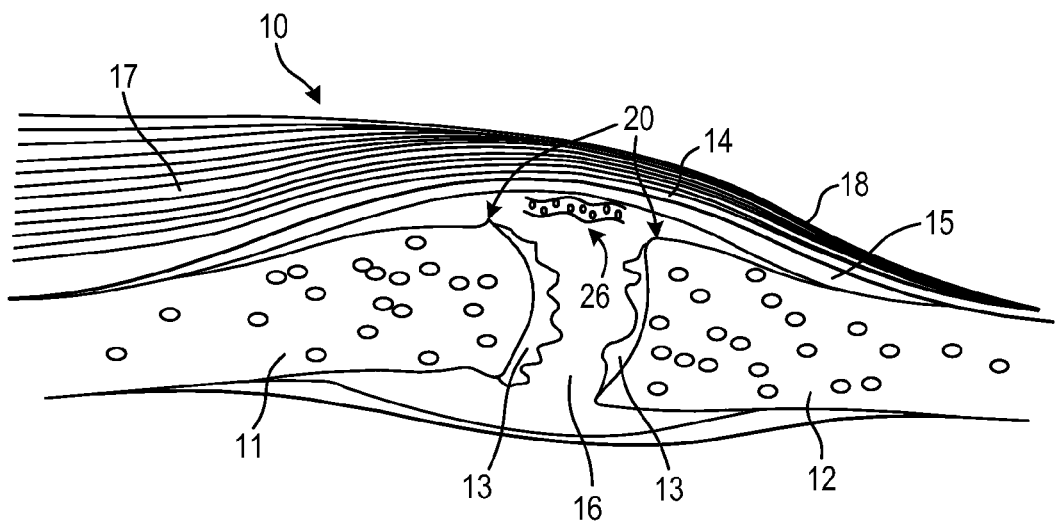
FIG. 2 illustrates a side sectional view of a joint affected by osteoarthritis and delivery of an embodiment of a flowable composition containing a therapeutic agent dispersed therein, which adheres and hardens to form the drug depot after it is implanted at the target tissue, in this case, a synovial joint.

FIG. 2 illustrates one embodiment of the effect of osteoarthritis on the joint 10. Osteoarthritis causes the cartilage 13 to become worn away from the ends of the bones 11 and 12. Fragments of cartilage may break off from the bones and become suspended in the synovial fluid 16. Bone spurs (20 in FIG. 2) may grow out from the edge of the bones 11 and 12. Osteoarthritis may also cause the synovial membrane 15 that produces a synovial fluid 16 to nourish and lubricate the cartilage 13 to produce an increased amount of synovial fluid 16. Altogether, the joint 10 may become swollen and/or feel stiff and sore. Muscles 17, connective tendons 18, and other tissue (e.g., ligaments) surround the joint capsule 14 and keep the bones 11 and 12 stable and allow the joint 10 to bend and move. However, symptoms become worse and debilitating as the disease progresses. To treat the diseased joint, the flowable composition can be administered locally at the target site utilizing a cannula or needle that penetrates beneath the skin to the target site. In this embodiment, the flowable composition comprises a therapeutic agent suspended in it and the flowable composition is sprayed near the target site (shown near the osteolytic lesions). In this embodiment, the flowable composition has adhering and hardening characteristics 26 and adheres and hardens into the drug depot in an area that does not interfere with movement of the joint and is away from the articular surfaces of the joint. As the synovial fluid contacts the harden depot, the therapeutic agent suspended therein is released.

In some embodiments, prior to administering the flowable composition, one can suction out the synovial fluid and then wash the joint with a saline solution or other physiologically neutral solution. The suctioning of fluids and addition of the physiologically neutral solution can be repeated any number of times for any length of time. The steps can occur simultaneously or as distinctly different steps. Not wishing to be bound to a particular hypothesis, it is believed that the synovial fluid of an inflamed joint contains a myriad of pro-inflammatory cytokines and other pro-inflammatory molecules. Washing out the inflamed joint removes most or all of these pro-inflammatory cytokines and other pro-inflammatory molecules and benefits the treatment regimens.

Although the joint site is shown, as described above, the flowable composition can be used to deliver a drug depot to any site beneath the skin, including, but not limited to, at least one muscle, ligament, tendon, cartilage, synovial joint, spinal disc, spinal foraminal space, near the spinal nerve root, facet joint, or spinal canal.

Confining Element

In some embodiments, a confining element such as a sheet, strip, ribbon, ring, balloon, tissue cavity, chamber or the like can be used to provide space for the flowable composition to be implanted so that the flowable composition can be confined at or near the target tissue site.

In some embodiments, the confining element may be a cavity created at the target tissue site that can be filled with the flowable composition containing the therapeutic agent before, during or after the medical and/or surgical procedure. In this way, the flowable composition will harden after instillation and the therapeutic agent will gradually be released from the drug depot over time.

Figure 3:
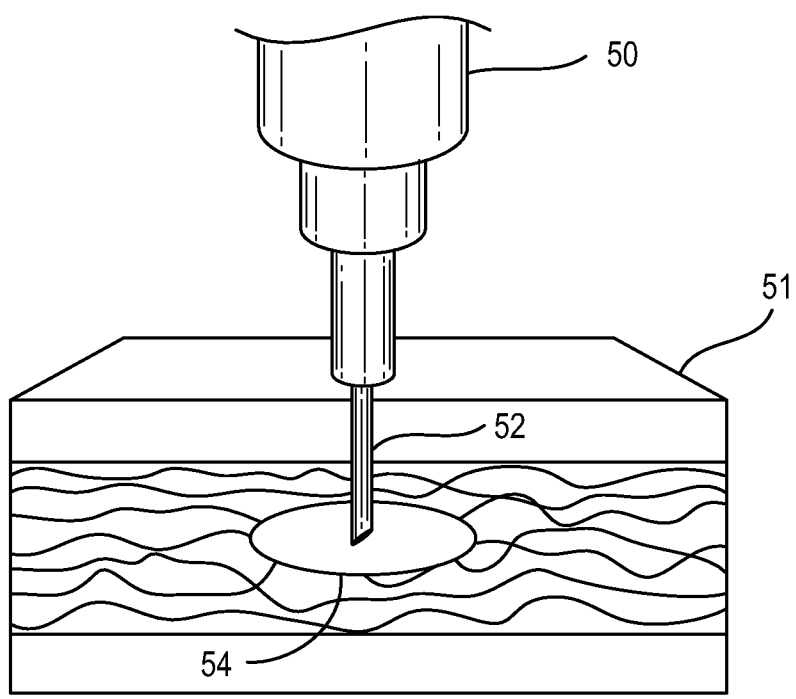
FIG. 3 illustrates a magnified view of a target tissue site having a cavity that the flowable composition can locally via a needle or cannula be administered thereto.

FIG. 3 illustrates a magnified view of an embodiment where the flowable composition is delivered by syringe 50 to a cavity in the target tissue site 54 via needle 52. The cavity in the target tissue site 54 confines the flowable composition and is beneath the skin 51 adjacent to the synovial membrane so that it does not interfere with movement of the joint.

Figure 4:
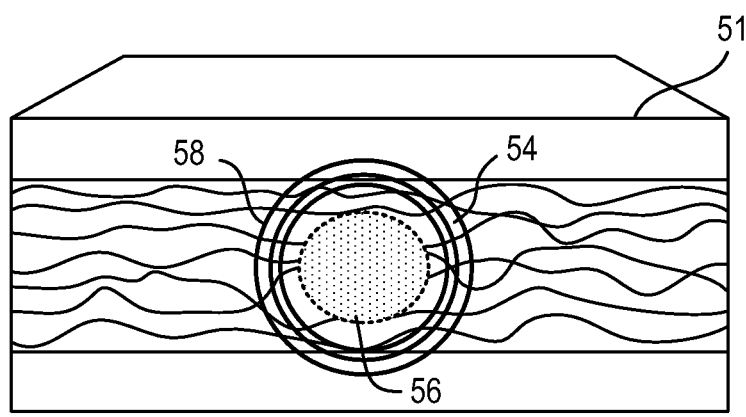
FIG. 4 illustrates a magnified view of a target tissue site after local administration of the flowable composition. In this illustrated embodiment, the flowable composition hardens to form a solid drug depot where the drug is released from the depot.

FIG. 4 illustrates a magnified view of a target tissue site beneath the skin 51 after local administration in the cavity 54 of the flowable composition. As time passes, the flowable composition hardens into the drug depot 56 as the flowable composition contacts bodily fluid, solvent contained in the flowable composition diffuses away, and/or the flowable composition reaches body temperature. In this illustrated embodiment, the flowable composition will harden at the target tissue site to form the drug depot and the drug will be released in a controlled manner 58.

In some embodiments, the confining element may be folded or in a compressed state and after deployment expands or unfolds. A port on the confining element created can be filled with the flowable composition containing the therapeutic agent before, during or after the medical and/or surgical procedure. In this way, the flowable composition will harden after instillation and the therapeutic agent will gradually be released from the drug depot over time by solvent-depletion, fluid exchange, degradation of the surface (e.g., thermal degradation), and/or diffusion through pores of the surface of the depot.

Figure 5:
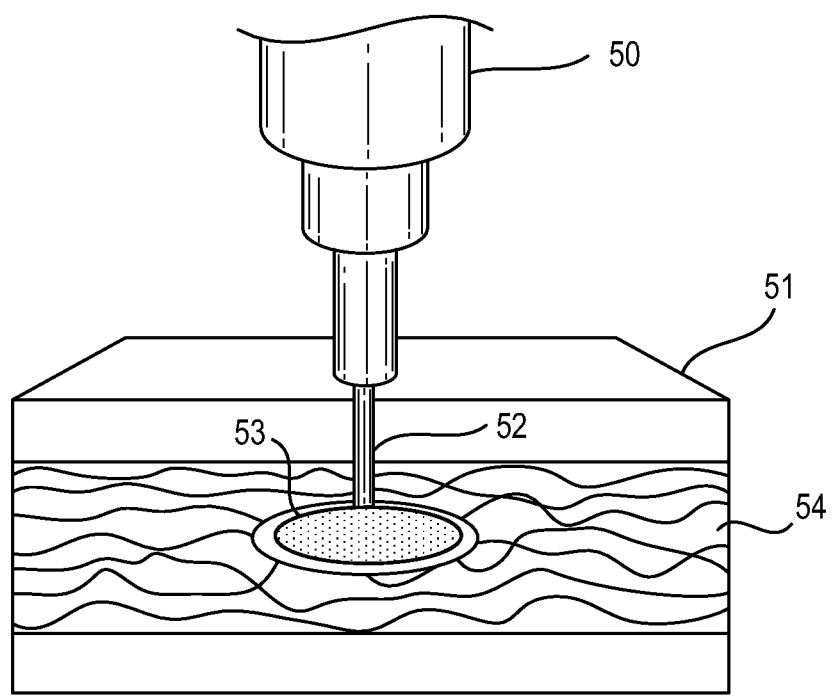
FIG. 5 illustrates a magnified view of a target tissue site containing a drug depot having a confining element (in this case a chamber) that can be used to fill the drug depot with the flowable composition containing the therapeutic agent.

FIG. 5 illustrates a magnified view of an embodiment where a target tissue site 54 beneath the skin 51 has a confining element (in this case a chamber of a drug depot in a compressed, or folded state) that the flowable composition can be used to fill the chamber 53 inside the drug depot. The flowable composition containing the therapeutic agent can be delivered by syringe 50 and needle 51 to fill the chamber 53. One can view this embodiment of the depot as a balloon in an unexpanded or compressed state. The balloon has a low profile whereby its height is minimized compared to its width and/or length. Even with the internal chamber filled, this depot does not interfere with the movement of the connective tissue within the joint when implanted at or near the joint membrane or when placed in an upper synovial bursa of the knee.

Figure 6:
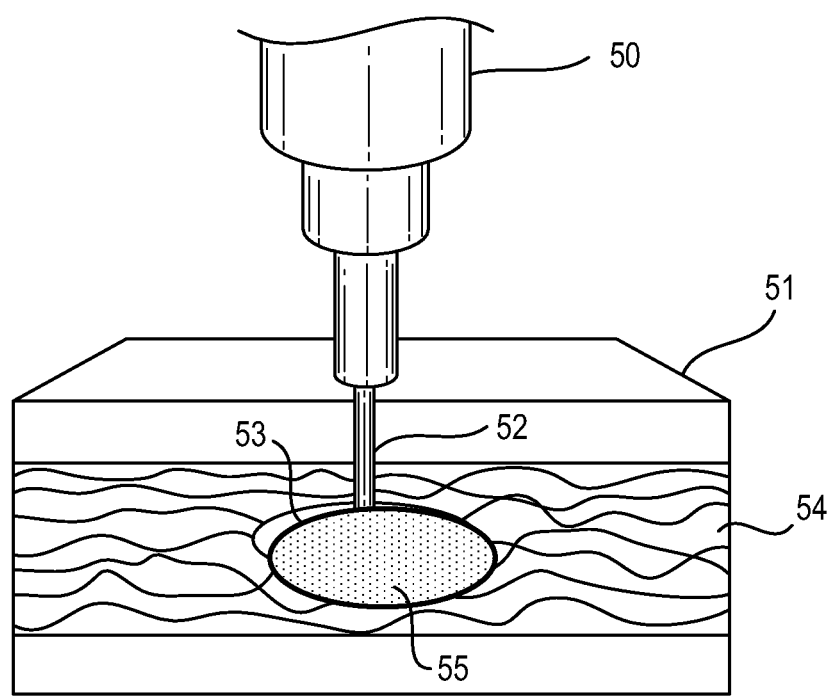
FIG. 6 illustrates a magnified view of a target tissue site containing a drug depot having a confining element (in this case a chamber) that is filled with the flowable composition containing the therapeutic agent.

FIG. 6 illustrates a magnified view of an embodiment where a target tissue site 54 beneath the skin 51 has a confining element (in this case a chamber 53 of a drug depot in an expanded state) filled with the flowable composition. The flowable composition containing the therapeutic agent can be delivered by syringe 50 and needle 51 to fill the chamber 53. In this illustrated embodiment, the chamber is expanded and filled with the flowable composition and the drug depot expands further holding the drug depot at a position away from a joint so that it does not interfere with movement.

Figure 7:
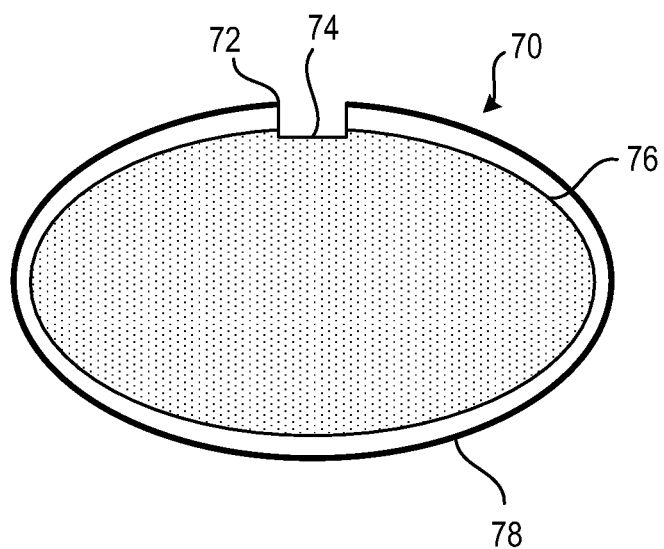
FIG. 7 is a side sectional view of an oval shaped drug depot that contains a confining element (in this case a chamber) for filing the therapeutic agent within the drug depot.

FIG. 7 is a side sectional view of an oval shaped drug depot 70 that has an exterior surface 78 that allows release of the therapeutic agent as fluid contacts the depot. The exterior surface of the depot comprises a channel 74 that allows the drug depot to be filled with the flowable composition. It will be understood that the drug depot may have a closure member to close channel 74. For convenience, in this embodiment, the channel is in an open position. The depot can be flat or have some curvature to it. In one embodiment, the depot is shaped to mimic the curvature of a synovial joint membrane. In this manner, the depot can be placed along the inside of the synovial joint membrane and not protrude or extend too much into the joint space. Thus, the depot does not interfere with the movement of the connective tissue within the joint. Alternatively, the depot can be placed on the outside of the synovial joint, attached to the membrane, and not project into the surrounding tissue. In this manner, the depot would not interfere with the movement of the tissue around the joint. When the depot is flat, it has flexibility to bend and take the shape in which it is positioned.

In various embodiments, the flowable composition is used to treat or manage pain, or other diseases or conditions of the patient. Pain includes acute pain and neuropathic pain. Acute pain refers to pain experienced when tissue is being damaged or is damaged (e.g., injury, infection, etc.). As contrasted to acute pain, neuropathic pain serves no beneficial purpose. Neuropathic pain results when pain associated with an injury or infection continues in an area once the injury or infection has resolved. Sciatica provides an example of pain that can transition from acute to neuropathic pain. Sciatica refers to pain associated with the sciatic nerve which runs from the lower part of the spinal cord (the lumbar region), down the back of the leg and to the foot. Sciatica generally begins with a herniated disc. The herniated disc itself leads to local immune system activation. The herniated disc also may damage the nerve root by pinching or compressing it, leading to additional immune system activation in the area.

The term "pain management medication" includes one or more therapeutic agents that are administered to prevent, alleviate or remove pain entirely. These include anti-inflammatory agents, muscle relaxants, analgesics, anesthetics, narcotics, and so forth, and combinations thereof.

In various embodiments, the flowable composition may have the therapeutic agent suspended therein and deployed around a targeted tissue site (e.g., a nerve root). The flowable composition keeps the therapeutic agent closely bound to target site (e.g., a nerve root) providing a therapeutically effective dosage of the therapeutic agent to the target site, with the dosage gradient rapidly falling off outside of the region of the flowable composition. The therapeutic agent is therefore tightly targeted to the desired tissue site.

In some embodiments, the drug depot is a solid implant that has a surface that is contoured to an inner surface of joint capsular tissue. The depot, which can be a low-profile structure (e.g., such as a sheet, ribbon, wafer, etc.) can be introduced through the joint capsule through a delivery cannula and thereafter manipulated to position a face of the sheet against the inner capsular wall. The sheet can then be attached or adhered in position.

In various embodiments, the low profile of the depot minimizes volume displacement if placed in the synovial space. The "low profile" shape of the depot means that the depot's height is minimized. The length and width of the depot can range from about 1 mm to about 35 mm. The height of the depot can range from about 0.1 mm to about 1.5 mm. Because the height is minimized as compared to the length and width, the depot's shape can be in the form of a sheet, ribbon, fiber, disc, thread, wafer, or other similar shapes. In one embodiment, the depot can have small voids randomly present throughout the depot, thus giving the appearance of a mesh, sponge, or similar item. When attached to the inside of the joint membrane or placed in the upper lateral gutter of the knee (the lateral gutter of the knee is the region posterior to the patella), this low profile depot allows for normal articulation of the joint.

Having now generally described the invention, the same may be more readily understood through the following reference to the following examples, which are provided by way of illustration and are not intended to limit the present invention unless specified.

EXAMPLES

The present application is more particularly described in the following examples which are intended for illustration purposes only, since numerous modifications and variations will be apparent to those skilled in the art.

Example 1

Production of a Solvent Depletion Depot

Poly(D,L-lactic acid) is prepared by simple polycondensation of lactic acid. Low molecular weight of poly(D,L-lactic acid) is dissolved in N-methyl-2-pyrrolidone (NMP) to give a 70:30 ratio of polymer to solvent. Dexamethasone is added to the polymer solution to give a 2% by weight dispersion of dexamethasone in the total mixture.

Example 2

A viscous gel material is prepared by heating 60% by weight of triacetin with 40% by weight of a 50:50 mixture of lactic acid:glycolic acid copolymer to 37° C. for twelve hours. The viscous gel is allowed to cool to room temperature while continuing mixing. Dexamethasone is added, while mixing continues, to the viscous gel in a ratio of 20:80 by weight dexamethasone:viscous gel. Mixing continues for approximately 5 minutes, then the mixture is allowed to remain at room temperature until just prior to use. Immediately prior to use, a 10% ethanol, 90% isotonic saline solution is added as an emulsifying agent while mixing. The emulsifying agent is approximately one-third of the total injectable depot gel.

Example 3

In-Vivo Study

Twenty-four mature rabbits undergo anterior cruciate ligament transection of the right knee to stimulate osteoarthritis. Six rabbits are used as negative controls. Six rabbits receive systemic injections of dexamethasone on a periodic basis. For six rabbits, 2 ml of the solvent depletion depot containing 2 wt % dexamethasone made as described above are loaded into a syringe with 22 gauge needle.

The needle is inserted through the skin, tissue, and synovial membrane of the knee joint. The liquid depot is injected to the knee joint. The solvent is allowed to dissipate, hardening the depot. Six rabbits have their injured knee washed with phosphate buffered saline for three minutes. Then 2 ml of the solvent depletion depot containing 2% dexamethasone is injected into the right knee using a 22 gauge needle. Three rabbits from each group are euthanized at three months. The remaining rabbits are euthanized at six months. Histology sections of the knee joints are compared and showed decreased inflammation for the dexamethasone groups.

Example 4

Production of a Thermosetting Depot

PEGs (m.w.=1000, 38.28 g, 38.23 mmole) is dissolved in 90 ml toluene. The toluene is distilled off to a final volume of 50 ml to remove water by azeotropic distillation. Carboxylic acid terminated PEG (CPEG) is prepared by mixing the PEG with excess amounts of glutaric anhydride (7.255 g, 80.39 mmole) in the presence of catalytic amount of glutaric acid (0.042 g, 0.40 mmole), stirring for 6 hours at 120° C. Dimethyl ether is added to the reaction mixture to precipitate out the CPEG. The CPEG is placed in vacuum for 48 hours to remove any residual solvent.

Epoxy terminated PEG (m.w.–600, 5.619 g, 9.36 mmole) is reacted with CPEG (11.50 g, 9.36 mmole) in toluene at 120° C. for 24 hours to prepare PEG with pendant hydroxyl groups (PEGH) along the PEG backbone.

D,L-lactide (19.2 g, 133.3 mmole) an glycolide (6.4 g, 55.1 mmole) is polymerized in situ on the preformed PEGH backbone for 24 hours at 130° C. using stannous octoate (76 µl, 0.187 mmole) as a catalyst. The graft copolymers are precipitated into excess ethyl ether, and the residual solvent is removed under vacuum.

Dexamethasone is added to the polymer solution to give a 2% by weight dispersion of dexamethasone in the total mixture.

Example 5

Polypropylene oxide-polyethylene oxide block copolymer (BASF, m.w. 12,000) is melt dried in vacuo at 100° C. for 4 hours. D,L-lactide (Boehringer Ingelheim) is added to the melt under nitrogen flush, followed by stannous octoate as a ring opening catalyst. After a reaction time of 4 hours, the melt is dissolved in toluene and precipitated in a large excess of hexane. Acrylation is carried out by adding triethylamine and acryloyl chloride in an argon atmosphere at 60° C. for 10 minutes. The hot, turbid reaction mixture is filtered, and the filtrate is added to a large excess of hexane. Vacuum filtration removes the hexane and dries the polymer. The polymer is dissolved in toluene again, and dexamethasone is added to the polymer solution to give a 2% by weight dispersion of dexamethasone in the total mixture. The polymer is again precipitated by adding excess hexane and then dried.

Example 6

In-Vivo Study

Twenty-four mature rabbits undergo anterior cruciate ligament transection of the right knee to stimulate osteoarthritis. Six rabbits are used as negative controls. Six rabbits receive systemic injections of dexamethasone on a periodic basis. For six rabbits, 2 ml of the thermosetting depot containing 2% dexamethasone made as described above are loaded into a syringe with 22 gauge needle.

The needle is inserted through the skin, tissue, and synovial membrane of the knee joint, and the liquid depot is injected to the knee joint. As the temperature of the liquid depot rises above the sol-to-gel transition temperature, a depot sets within the joint of the animal. Six rabbits have their injured knee washed with phosphate buffered saline for three minutes. Then 2 ml of the thermosetting depot containing 2% dexamethasone is injected into the right knee using a 22 gauge needle. Three rabbits from each group are euthanized at three months. The remaining rabbits are euthanized at six months. Histology sections of the knee joints are compared and showed decreased inflammation for the dexamethasone groups.

It will be apparent to those skilled in the art that various modifications and variations can be made to various embodiments described herein without departing from the spirit or scope of the teachings herein. Thus, it is intended that various embodiments cover other modifications and variations of various embodiments within the scope of the present teachings.

What is claimed is:

1. A flowable composition for delivering a therapeutic agent at or near a target tissue site beneath the skin of a patient, the flowable composition comprising (i) a solvent; (ii) an effective amount of the therapeutic agent; and (iii) a polymer, the flowable composition being capable of hardening to form a drug depot at a physiological temperature or as solvent contacts bodily fluid at or near the target tissue site, wherein the drug depot has a pre-dosed modulus of elasticity of about $2 \times 10^4$ to about $2 \times 10^5$ dynes/cm$^2$, and is capable of releasing the therapeutic agent over a period of at least one day and the target tissue site comprises at least one muscle, ligament, tendon, cartilage, spinal disc, spinal foraminal space near the spinal nerve root, facet or synovial joint, or spinal canal, and the solvent comprises polyethylene glycol with pendant hydroxyl groups (PEGH), the polymer comprises (poly(d,l-lactide-co-glycolide), and the drug depot comprises a porosity of about 25-85%, and the flowable composition is disposed in a deployable balloon.

2. A flowable composition according to claim 1, wherein the flowable composition is a gel that hardens to form a solid drug depot.

3. A flowable composition for delivering a therapeutic agent according to claim 2, wherein the gel further comprises a bolus dose of the therapeutic agent suspended in the gel to provide an immediate release of the therapeutic agent and the effective amount of the therapeutic agent is encapsulated in a plurality of microparticles, microspheres, microcapsules, and/or microfibers to provide sustained release of the therapeutic agent over time.

4. A flowable composition according to claim 1, wherein the flowable composition comprises a solvent that diffuses away as the flowable composition hardens to form the drug depot.

5. A flowable composition for delivering a therapeutic agent according to claim 1, wherein the flowable composition is a liquid at room temperature and hardens at physiological temperature to form the drug depot.

6. A flowable composition for delivering a therapeutic agent according to claim 1, wherein the therapeutic agent comprises an anti-inflammatory agent, an analgesic agent, a skeletal muscle relaxant, an osteoinductive anabolic growth factor, an anti-catabolic growth factor or a combination thereof.

7. A flowable composition for delivering a therapeutic agent according to claim 1, wherein the therapeutic agent is encapsulated in a plurality of microparticles, microspheres, microcapsules, and/or microfibers suspended in the flowable composition.

8. A flowable composition for delivering a therapeutic agent according to claim 1, wherein the composition comprises a radiographic marker adapted to assist in radiographic imaging.

9. A flowable composition for delivering a therapeutic agent according to claim 1, wherein the drug depot has a post-dosed modulus of elasticity of about $2 \times 10^5$ to about $5 \times 10^5$ dynes/cm$^2$.

10. A flowable composition for delivering a therapeutic agent according to claim 1, wherein the flowable composition comprises a pore-forming additive comprising hydroxylpropylcellulose.

11. A flowable composition for delivering a therapeutic agent according to claim 1, wherein the flowable composition comprises pore diameters of about 4 to about 1000 microns before hardening and the flowable composition comprises pore diameters of about 3 to about 500 microns after hardening into the drug depot.

12. A flowable composition for delivering a therapeutic agent according to claim 1, wherein the polymer (poly(d,l-lactide-co-glycolide) comprises about 30 wt % to about 60 wt % of the flowable composition.

13. A flowable composition for delivering a therapeutic agent according to claim 1, wherein the balloon is expandable when the flowable composition is disposed in the balloon.

* * * * *